US008648015B2

(12) United States Patent
Estell et al.

(10) Patent No.: US 8,648,015 B2
(45) Date of Patent: Feb. 11, 2014

(54) SYSTEMATIC EVALUATION OF SEQUENCE AND ACTIVITY RELATIONSHIPS USING SITE EVALUATION LIBRARIES FOR ENGINEERING MULTIPLE PROPERTIES

(75) Inventors: David A. Estell, San Francisco, CA (US); Wolfgang Aehle, Zwingenberg (DE)

(73) Assignee: Danisco US Inc., Palo Alto, CA (US)

( * ) Notice: Subject to any disclaimer, the term of this patent is extended or adjusted under 35 U.S.C. 154(b) by 297 days.

(21) Appl. No.: 12/778,915

(22) Filed: May 12, 2010

(65) Prior Publication Data

US 2011/0082048 A1    Apr. 7, 2011

Related U.S. Application Data

(63) Continuation of application No. 11/821,468, filed on Jun. 22, 2007, now abandoned.

(60) Provisional application No. 60/816,202, filed on Jun. 23, 2006, provisional application No. 60/933,312, filed on Jun. 6, 2007.

(51) Int. Cl.
*C40B 20/04* (2006.01)
*C40B 40/02* (2006.01)

(52) U.S. Cl.
USPC ............ 506/4; 506/2; 506/12; 506/11; 506/7; 506/9

(58) Field of Classification Search
USPC ..................... 506/2, 4, 7, 9, 11, 12
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| RE34,606 E | 5/1994 | Estell et al. | |
| 5,322,770 A | 6/1994 | Gelfand | |
| 5,700,676 A | 12/1997 | Bott et al. | |
| 5,955,340 A | 9/1999 | Bott et al. | |
| 6,312,936 B1 | 11/2001 | Poulose et al. | |
| 6,376,450 B1 | 4/2002 | Ghosh et al. | |
| 6,482,628 B1 | 11/2002 | Poulose et al. | |
| 6,582,914 B1 | 6/2003 | Caldwell et al. | |
| 6,605,458 B1 | 8/2003 | Hansen et al. | |
| 6,682,924 B1 | 1/2004 | Sierkstra et al. | |
| 2008/0063774 A1* | 3/2008 | Aehle et al. ................... | 426/531 |
| 2008/0145353 A1 | 6/2008 | Amin et al. | |
| 2008/0293610 A1 | 11/2008 | Shaw et al. | |

FOREIGN PATENT DOCUMENTS

| | | | |
|---|---|---|---|
| WO | WO 92/21760 A1 | 12/1992 | |
| WO | WO 95/23221 A1 | 8/1995 | |
| WO | WO 97/07770 A1 | 3/1997 | |
| WO | 9920771 A2 | 4/1999 | |
| WO | WO 99/34011 A2 | 7/1999 | |
| WO | WO 02/103009 A2 | 12/2002 | |
| WO | 03062381 A2 | 7/2003 | |
| WO | WO 2005/005654 A1 | 1/2005 | |
| WO | WO 2005/040408 A1 | 5/2005 | |
| WO | WO 2005/052146 A2 | 6/2005 | |
| WO | WO 2005/052161 A2 | 6/2005 | |
| WO | WO 2006/023635 A2 | 3/2006 | |

OTHER PUBLICATIONS

Aharoni, A. et al. "High-throughput screens and selections of enzyme-encoding genes." *Current Opinion in Chemical Biology* 9(2): 210-216, Apr. 2005.
Altschul, S.F. et al. "Local alignment statistics." *Methods Enzymol* 266: 460-80, 1996.
Altschul, S.F. et al. "Basic local alignment search tool." *J. Mol. Biol* 215(3): 403-410, 1990.
Bloom, J.D. et al. "Protein stability promotes evolvability." *Proc. Natl. Acad. Sci. U.S.A* 103(15): 5869-74, Apr. 11, 2006.
Bloom, J.D. et al. "Evolving strategies for enzyme engineering." *Current Opinion in Structural Biology* 15(4): 447-452, Aug. 2005.
Bornscheuer, U.T. et al. "Directed evolution of an esterase for the stereoselective resolution of a key intermediate in the synthesis of epothilones." *Biotechnology and Bioengineering* 58(5): 554-559, 1998.
Bornscheuer, U.T. et al. "Optimizing lipases and related enzymes for efficient application." *Trends in Biotechnology* 20(10): 433-437, Oct. 1, 2002.
Cozzini, P. et al. "Free Energy of Ligand Binding to Protein: Evaluation of the Contribution of Water Molecules by Computational Methods." *Current Medicinal Chemistry* 11(23): 3093-3118, Dec. 2004.
DelMar, E.G. et al. "A sensitive new substrate for chymotrypsin." *Analytical Biochemistry* 99(2): 316-320, Nov. 1, 1979.
Devereux, P. et al. "A comprehensive set of sequence analysis programs for the VAX." *Nucl. Acids Res* 12: 387-395, 1984.
Duckworth, A.W. et al. "Phylogenetic diversity of soda lake alkaliphiles." *FEMS Microbiology Ecology* 19(3): 181-191, 1996.
Dynan, W.S. et al. "Control of eukaryotic messenger RNA synthesis by sequence-specific DNA-binding proteins." *Nature* 316(6031): 774-778, 1985.
Edgar, R.C. "MUSCLE: multiple sequence alignment with high accuracy and high throughput." *Nucleic Acids Research* 32(5): 1792-1797, 2004.
Estell, D.A. et al. "Site-directed mutagenesis of the active site of Subtilisin BPN," In *The World Biotech Report 1984: The Proceedings of Biotech 84*, USA, 2: USA:pp. 181-187. Pinner, UK: Online Publications, 1984.
Feng, D.F. et al. "Progressive sequence alignment as a prerequisite to correct phylogenetic trees." *J. Mol. Evol* 25(4): 351-360, 1987.
Ferrari, E. et al. "Genetics." In *Bacillus*, edited by C.R. Harwood, pp. 57-72. Biotechnology Handbooks 2. New York: Plenum Press, 1989.

(Continued)

*Primary Examiner* — Teresa Wessendorf
(74) *Attorney, Agent, or Firm* — Danisco US Inc.

(57) ABSTRACT

The present invention provides methods for protein engineering. Specifically, the invention provides methods utilizing site evaluation libraries to design libraries that optimize two or more properties of a protein.

2 Claims, 2 Drawing Sheets

(56) References Cited

OTHER PUBLICATIONS

Guo, H.H. et al. "Protein tolerance to random amino acid change." *Proc. Natl. Acad. Sci. U.S.A* 101(25): 9205-10, Jun. 22, 2004.

Higgins, D.G. et al. "Fast and sensitive multiple alignment sequence on a microcomputer." *CABIOS* 5(2): 151-153, 1989.

Kalisz, H.M. "Microbial proteinases." *Advances in Biochemical Engineering/Biotechnology* 36: 1-65, 1988.

Karlin, S. et al. "Applications and statistics for multiple high-scoring segments in molecular sequences." *Proc. Natl. Acad. Sci. USA* 90(12): 5873-7, Jun. 15, 1993.

Kato, R. et al. "Novel Strategy for Protein Exploration: High-throughput Screening Assisted with Fuzzy Neural Network." *Journal of Molecular Biology* 351(3): 683-692, Aug. 19, 2005.

Lancet, D. et al. "Probability model for molecular recognition in biological receptor repertoires: significance to the olfactory system." *Proc. Natl. Acad. Sci. U.S.A* 90(8): 3715-9, Apr. 15, 1993.

Lu, S.M. et al. "Predicting the reactivity of proteins from their sequence alone: Kazal family of protein inhibitors of serine proteinases." *Proc. Natl. Acad. Sci. U.S.A* 98(4): 1410-5, Feb. 13, 2001.

Needleman, S.B. et al. "A general method applicable to the search for similarities in the amino acid sequence of two proteins." *J. Mol. Biol* 48(3): 443-53, Mar. 1970.

Olsen, M. et al. "High-throughput screening of enzyme libraries." *Current Opinion in Biotechnology* 11(4): 331-337, Aug. 1, 2000.

Pearson, W.R. et al. "Improved Tools for Biological Sequence Comparison." *Proc. Natl. Acad. Sci. USA* 85(8): 2444-2448, Apr. 15, 1988.

Pierce, N.A. et al. "Protein design is NP-hard." *Protein Engineering* 15(10): 779-82, Oct. 2002.

Rawlings, N.D. et al. "MEROPS: the peptidase database." *Nucl. Acids Res.* 34(Suppl. 1): D270-272, Jan. 1, 2006.

Reetz, M.T. et al. "Expanding the Range of Substrate Acceptance of Enzymes: Combinatorial Active-Site Saturation Test." *Angewandte Chemie International Edition* 44(27): 4192-4196, 2005.

Rungpragayphan, S. et al. "PCR-linked in vitro expression: a novel system for high-throughput construction and screening of protein libraries." *FEBS Letters* 540(1-3): 147-150, Apr. 10, 2003.

Sandberg, W.S. et al. "Engineering multiple properties of a protein by combinatorial mutagenesis." *Proc. Natl. Acad. Sci. U.S.A* 90(18): 8367-71, Sep. 15, 1993.

Schmidt-Dannert, C. et al. "Molecular breeding of carotenoid biosynthetic pathways." *Nat Biotech* 18(7): 750-753, Jul. 2000.

Smith, T.F. et al. "Comparison of biosequences." *Adv. Appl. Math* 2: 482-489, 1981.

Soumillion, P. et al. "Novel concepts for selection of catalytic activity." *Current Opinion in Biotechnology* 12(4): 387-394, Aug. 1, 2001.

Varadarajan, N. et al. "Engineering of protease variants exhibiting high catalytic activity and exquisite substrate selectivity." *Proc. Natl. Acad. Sci. U.S.A* 102(19): 6855-60, May 10, 2005.

Wells, J A et al. "Cassette mutagenesis: an efficient method for generation of multiple mutations at defined sites." *Gene* 34(2-3): 315-23, 1985.

International Search Report and the Written Opinion of the International Searching Authority for International Application No. PCT/US07/014556 dated Dec. 17, 2007.

Cohen, et al., "In vitro enzyme evolution: the screening challenge of isolating the one in a million", Trends Biotechnol, 2001, 19:507-10.

Rubingh, "Protein engineering from a bioindustrial point of view", Curr Opin Biotechnol, 1997, 8:417-22.

Wells, et al., "Designing substrate specificity by protein engineering of electrostatic interactions", Proc Natl Acad Sci, 1987, 84:1219-23.

* cited by examiner

SEQUENCE LISTING

<160> NUMBER OF SEQ ID NOS: 2

<210> SEQ ID NO 1
<211> LENGTH: 1488
<212> TYPE: DNA
<213> ORGANISM: Artificial Sequence
<220> FEATURE:
<223> OTHER INFORMATION: Synthetic ASP DNA Sequence

<400> SEQUENCE: 1

```
atgacaccac gaactgtcac aagagctctg gctgtggcaa cagcagctgc tacactcttg      60 gctggggta tggcagcaca agctaacgaa ccggctcctc caggatctgc atcagcccct      120
ccacgattag ctgaaaaact tgaccctgac ttacttgaag caatggaacg cgatctgggg      180
ttagatgcag aggaagcagc tgcaacgtta gcttttcagc atgacgcagc tgaaacggga      240
gaggctcttg ctgaggaact cgacgaagat ttcgcgggca cgtgggttga agatgatgtg      300
ctgtatgttg caaccactga tgaagatgct gttgaagaag tcgaaggcga aggagcaact      360
gctgtgactg ttgagcattc tcttgctgat ttagaggcgt ggaagacggt tttggatgct      420
gcgctggagg gtcatgatga tgtgcctacg tggtacgtcg acgtgcctac gaattcggta      480
gtcgttgctg taaaggcagg agcgcaggat gtagctgcag gacttgtgga aggcgctgat      540
gtgccatcag atgcggtcac ttttgtagaa acggacgaaa cgcctagaac gatgttcgac      600
gtaattggag gcaacgcata tactattggc ggccggtcta gatgttctat cggattcgca      660
gtaaacggtg gcttcattac tgccggtcac tgcggaagaa caggagccac tactgccaat      720
ccgactggca catttgcagg tagctcgttt ccgggaaatg attatgcatt cgtccgaaca      780
ggggcaggag taaatttgct tgcccaagtc aataactact cggcggcag agtccaagta      840 gcaggacata cggccgcacc agttggatct gctgtatgcc gctcaggtag cactacaggt      900
tggcattgcg gaactatcac ggcgctgaat tcgtctgtca cgtatccaga gggaacagtc      960
cgaggactta tccgcacgac ggtttgtgcc gaaccaggtg atagcggagg tagccttta     1020 gcgggaaatc aagcccaagg tgtcacgtca ggtggttctg gaaattgtcg gacggggga     1080 acaacattct ttcaaccagt caacccgatt ttgcaggctt acggcctgag aatgattacg     1140
actgactctg gaagttcccc tgctccagca cctacatcat gtacaggcta cgcaagaacg     1200
ttcacaggaa ccctcgcagc aggaagagca gcagctcaac cgaacggtag ctatgttcag     1260
gtcaaccgga gcggtacaca ttccgtctgt ctcaatggac ctagcggtgc ggactttgat     1320
ttgtatgtgc agcgatggaa tggcagtagc tgggtaaccg tcgctcaatc gacatcgccg     1380
ggaagcaatg aaaccattac gtaccgcgga aatgctggat attatcgcta cgtggttaac     1440
gctgcgtcag gatcaggagc ttacacaatg ggactcaccc tccctga                   1488
```

-continued

```
<210> SEQ ID NO 2
<211> LENGTH: 189
<212> TYPE: PRT
<213> ORGANISM: Cellumonas strain 69B4

<400> SEQUENCE: 2

Phe Asp Val Ile Gly Gly Asn Ala Tyr Thr Ile Gly Gly Arg Ser Arg
1               5                   10                  15

Cys Ser Ile Gly Phe Ala Val Asn Gly Gly Phe Ile Thr Ala Gly His
            20                  25                  30

Cys Gly Arg Thr Gly Ala Thr Thr Ala Asn Pro Thr Gly Thr Phe Ala
        35                  40                  45

Gly Ser Ser Phe Pro Gly Asn Asp Tyr Ala Phe Val Arg Thr Gly Ala
    50                  55                  60

Gly Val Asn Leu Leu Ala Gln Val Asn Asn Tyr Ser Gly Gly Arg Val
65                  70                  75                  80

Gln Val Ala Gly His Thr Ala Ala Pro Val Gly Ser Ala Val Cys Arg
                85                  90                  95

Ser Gly Ser Thr Thr Gly Trp His Cys Gly Thr Ile Thr Ala Leu Asn
            100                 105                 110

Ser Ser Val Thr Tyr Pro Glu Gly Thr Val Arg Gly Leu Ile Arg Thr
            115                 120                 125

Thr Val Cys Ala Glu Pro Gly Asp Ser Gly Gly Ser Leu Leu Ala Gly
    130                 135                 140

Asn Gln Ala Gln Gly Val Thr Ser Gly Gly Ser Gly Asn Cys Arg Thr
145                 150                 155                 160

Gly Gly Thr Thr Phe Phe Gln Pro Val Asn Pro Ile Leu Gln Ala Tyr
                165                 170                 175

Gly Leu Arg Met Ile Thr Thr Asp Ser Gly Ser Ser Pro
            180                 185
```

SYSTEMATIC EVALUATION OF SEQUENCE AND ACTIVITY RELATIONSHIPS USING SITE EVALUATION LIBRARIES FOR ENGINEERING MULTIPLE PROPERTIES

The present application is a continuation of U.S. patent application Ser. No. 11/821,468, filed Jun. 22, 2007, now abandoned, which claims the benefit of U.S. Provisional Patent Application Ser. No. 60/816,202, filed Jun. 23, 2006, and U.S. Provisional Patent Application Ser. No. 60/933,312, filed Jun. 6, 2007, which are herein incorporated by reference.

FIELD OF THE INVENTION

The present invention provides methods for protein engineering. Specifically, the invention provides methods utilizing site evaluation libraries.

SEQUENCE LISTING

The sequence listing submitted via EFS in compliance with 37 C.F.R. §1.52(e)(5) is incorporated herein by reference. The sequence listing text file submitted via EFS contains the file "30912C1_SequenceListing", created on Oct. 25, 2010, which is 4,263 bytes in size.

BACKGROUND OF THE INVENTION

Various protein engineering methods are known to those in the art. In general, proteins are modified in order to obtain desired protein properties. In most methods, the nucleotide sequence of a cloned gene encoding a protein is mutated and the modified gene is expressed to produce mutants, which are screened for activities of interest. Often, the mutant properties are compared with the properties of wild-type protein.

Historically, the protein design process has been approached as equivalent to the problem of finding in all of protein space the one best sequence for the desired application. This problem is extremely difficult and is "NP hard." In complexity theory, problems defined as being in class P, are considered easy and efficient, polynomial-time algorithms exist for their solution. NP-hard problems are problems for which efficient polynomial-time algorithms are not currently known, and if any NP-hard problem could be solved, all NP-hard problems could be solved (See e.g., Pierce and Winfree, Protein Engineer., 15:779-782 [2002]). Current strategies for building and screening libraries generally involve generating protein sequence diversity randomly across the whole sequence or in controlled random fashion at defined positions within the protein. These libraries generally have a large number of members that are "negative" with respect to the primary property of interest, and require large numbers be screened in order to find the relatively small numbers of positive mutations. Generally, negative mutations are ignored, and sequence information is only obtained for the positive members.

Saturation mutagenesis (Estell et al., in World Biotech Report 1984, vol. 2: USA, Online Publications, London [1984], pages 181-187; and Wells et al., Gene 34:315-323 [1985]) one technique that can be used to search protein space for mutations that optimize several properties in a protein. Several groups have developed strategies for identifying sites to be changed by saturation mutagenesis (Reetz et al., Angew. Chem. Int. Edn., 44:4192-4196 [2005]; Kato et al., J. Mol. Biol., 351:683-692 [2005]; and Sandberg et al., Proc. Natl. Acad. Sci., 90:8367-8371 [1993]), but no general system for site identification has been proposed.

In addition, because most protein engineering methods produce a great number of amino acid mutation options, screening of a large number of variants generally is required to produce a desired protein property. Generally, screening is repeated over and over to produce a beneficial variant. Thus, most methods are laborious and time-consuming. There is a continuing need in the art for protein engineering methods that are efficient and produce the desired results.

SUMMARY OF THE INVENTION

The present invention provides methods for protein engineering. Specifically, the invention provides methods utilizing site evaluation libraries. In particular, the present invention provides means to use information obtained about a number of desired properties, in order to rationally and efficiently design libraries that will optimize those properties. In some embodiments, the present invention provides means to design libraries that are improved for at least two desired properties.

The present invention provides means to identify positions within an amino acid sequences of a protein that are relevant in improving desired properties of the protein. In some particularly preferred embodiments, the present invention provides means to determine which mutations are desirable in order to produce proteins with these desired properties, as well as improved properties. In some additional particularly preferred embodiments, the present invention provides means to identify amino acid positions and mutations that have improvements of a particular percentage better than the wild-type protein (e.g., better than 110% of the wild-type for one property). In still further preferred embodiments, the present invention provides means to identify mutations that provide at least one much improved property and at least one additional property that is not significantly worse than the wild-type protein (e.g., better than 110% of wild-type for one property, yet not worse than 90% of wild-type for another property). In yet further preferred embodiments, libraries are constructed based on this information. In some embodiments, the libraries are constructed using all of the identified mutations, while in some other embodiments, the libraries are constructed using a subset of the identified mutations. Indeed, it is not intended that the libraries be constrained to any particular number and/or type of mutations.

The present invention provides methods for protein engineering comprising the steps of: providing a library of protein variants; testing the library of protein variants for at least one property of interest in a test of interest; identifying a range of values for said the at least one property of interest; identifying a minimum within the range of values that is associated with a favorable outcome in the test of interest; and providing a plurality of protein variants having at least one mutation above said minimum in the range of the at least one property of interest, thereby providing a library of protein variants comprising at least one mutation, and wherein the library is enriched in members having a favorable outcome in the test of interest. In some embodiments, the favorable outcome corresponds to a value of greater than 50%, 60%, 70%, 80%, 90%, or 95% of a maximal value observed in the test set forth in the first step above. In some alternative embodiments, more than one test of interest is used in the methods of the present invention. In some preferred embodiments, the protein is an enzyme. In some particularly preferred embodiments, the enzyme is selected from proteases, transferases, metalloproteases, esterases, amylases, cellulases, oxidases, cutinases, and lipases.

The present invention also provides methods for protein engineering comprising the steps of: providing a library of protein variants; testing the library of protein variants for at least two properties of interest in a test of interest; identifying a range of values for the at least two properties of interest; identifying a minimum within the range of values that is associated with a favorable outcome in the test of interest; and providing a plurality of protein variants above the minimum of the range of the at least two properties of interest, thereby providing a library of protein variants enriched in members having the favorable outcome in the test of interest. The method of Claim 5, wherein the favorable outcome corresponds to a value of greater than 50%, 60%, 70%, 80%, 90%, or 95% of a maximal value observed in the test set forth in the first step above. In some preferred embodiments, the protein is an enzyme. In some particularly preferred embodiments, the enzyme is selected from proteases, transferases, metalloproteases, esterases, amylases, cellulases, oxidases, cutinases, and lipases.

The present invention also provides methods for protein engineering comprising the steps of: providing a wild-type protein and a library of protein variants of the wild-type protein; testing the library of protein variants and the wild-type protein for at least one property of interest in a test of interest; identifying a range of values for the at least one property of interest; identifying a minimum within the range of values that is associated with a favorable outcome in the test of interest; identifying the protein variants having a favorable outcome as compared to the results obtained for the wild-type, wherein the favorable outcome is an improved property of interest; and providing a plurality of protein variants above the minimum of the range of the at least one property of interest, thereby providing a library of improved protein variants enriched in members having the favorable outcome in the test of interest. In some preferred embodiments, the methods further comprise the step of determining the performance index, wherein the performance index is determined by dividing the value obtained for each of the improved protein variants and the value obtained for the wild-type protein. In some particularly preferred embodiments, the methods further comprise the step of identifying the improved protein variants, wherein the improved protein variants achieve performance index values greater than 1.1 in the test of interest. In some additional embodiments, the protein is an enzyme. In some particularly preferred embodiments, the enzyme is selected from proteases, transferases, metalloproteases, esterases, amylases, cellulases, oxidases, cutinases, and lipases. In some alternative embodiments, the protein is selected from antibodies and growth factors. In still additional preferred embodiments, the wild-type protein is a mature form an enzyme selected from proteases, transferases, metalloproteases, esterases, amylases, cellulases, oxidases, cutinases, and lipases. In some preferred embodiments, the property of interest is selected from charge, wash performance, hard surface cleaning performance, thermal stability, storage stability, detergent stability, substrate binding, enzyme inhibition, expression level, reaction rate, and substrate degradation. In some embodiments, the wild-type protein and the protein variant are components of at least one detergent composition. In some preferred embodiments, wash performance is tested in a detergent composition formulated into a powdered or liquid detergent having a pH of between 5 and 12.0.

The present invention also provides methods for producing an improved variant of a parent protein within a protein fold, comprising: assaying multiple variants of a test protein within the protein fold spanning a range of a property of interest in an assay of interest; identifying a minimum within the range of the property of interest that is associated with a favorable outcome in the assay of interest; assaying a parent protein of the protein fold in the assay of interest; and producing an improved variant of the parent protein by introducing an amino acid substitution is the parent protein such that the improved variant is above the minimum of the range of the property of interest. In some preferred embodiments, the parent protein and the test protein are different. In some embodiments, the methods further comprise the step of determining the performance index, wherein the performance index is determined by dividing the value obtained for the improved protein variant and the value obtained for the parent protein. In some embodiments, the test proteins and the parent proteins are enzymes. In some particularly preferred embodiments, the enzymes are selected from proteases, transferases, metalloproteases, esterases, amylases, cellulases, oxidases, cutinases, and lipases. In some alternative embodiments, the test and parent proteins are selected from antibodies and growth factors. In still additional preferred embodiments, the parent protein is a mature form an enzyme selected from proteases, transferases, metalloproteases, esterases, amylases, cellulases, oxidases, cutinases, and lipases. In some preferred embodiments, the property of interest is selected from charge, wash performance, hard surface cleaning performance, thermal stability, storage stability, detergent stability, substrate binding, enzyme inhibition, expression level, reaction rate, and substrate degradation. In some embodiments, the test and parent proteins are components of at least one detergent composition. In some alternative embodiment, the improved protein variant is a component of a detergent composition. In some preferred embodiments, wash performance is tested in a detergent composition formulated into a powdered or liquid detergent having a pH of between 5 and 12.0.

DESCRIPTION OF THE INVENTION

Figure 1:
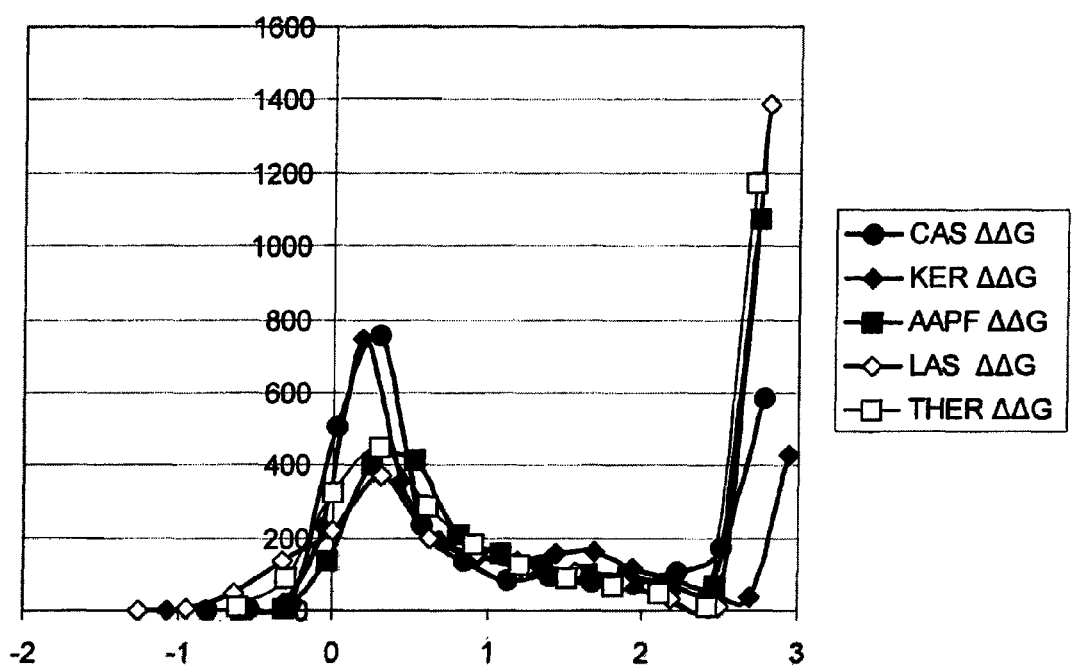
FIG. 1 provides the distributions of the 2851 $\Delta\Delta G_{app}$ values obtained for each property.

The present invention provides methods for protein engineering. Specifically, the invention provides methods utilizing site evaluation libraries.

For practical purposes, it is not usually necessary to find the best sequence in a protein space in order to create a protein that is optimum for a particular application. For most applications, the problem to be solved is to identify at least one protein sequence that meets or exceeds the minimum value required for a number of properties. This requires knowledge of mutations that are good for a particular property, as well as knowledge of those mutations that are bad for any of the desired properties. The present invention provides means to meet the goal by identifying those positions in the protein that can be altered to improve the primary property and keep the values for other properties within desired limits.

The present invention provides means to evaluate all positions in a protein for all the properties of interest by building "site evaluation libraries" at each site. In preferred embodiments, these libraries contain 9-19 mutations at each position, and are used to evaluate each position for use in engineering the protein and constructing libraries. Each property is measured relative to the parent enzyme and an apparent free energy difference for each mutant vs. wild type is calculated. These delta delta G ("i.e., ΔΔG") apparent values are then used to determine additivity.

An ideal way to analyze variants would be through the difference in free energy for the variant versus the parent protein in the process of interest. The Gibbs Free Energy for a process represents the maximum amount of work that can be performed by a system. The change in Free energy relative to the parent enzyme (ΔΔG) is given as follows;

$$\Delta\Delta G = -RT \ln(k_{variant}/k_{parent})$$

where $k_{variant}$ is the rate constant for the variant enzyme, and $k_{parent}$ is the rate constant for the parent enzyme, R is the Gas law constant and T is the absolute temperature. Most assays are not constructed to allow determination of true Free Energies, so we utilized a quantity $$\Delta\Delta G_{app} = -RT \ln(P_{variant}/P_{parent})$$

where $P_{variant}$ is the performance value for the variant and $P_{parent}$ is the performance value for the parent enzyme under the same conditions. The $\Delta\Delta G_{app}$ values may be expected to behave in a similar fashion as to ΔΔG for data distributions and additivity. However, since ΔΔG is the maximum amount of work that can be carried out by the variant compared to the parent enzyme, the quantity $\Delta\Delta G_{app}$ will generally underestimate the ΔΔG and lead to results that appear synergistic in that the properties of two additive positions may be greater than the value predicted by adding their $\Delta\Delta G_{app}$ values together.

The methods of the present invention used to design efficient libraries that were used to engineer multiple properties in parallel. Although "ASP," a 189 amino acid serine protease is described herein, the methods apply to any protein of interest for engineering. ASP protease is in the S1E family (See e.g., Rawlings et al., Nucleic Acids Res., 34:D270-D272 [2006]) of serine proteases, and is a homolog of the streptogrisins. The mature serine protease enzyme derived from Cellulomonas strain 69B4 (DSM 983316035) is 189 amino acids long (SEQ ID NO:2), with a catalytic triad consisting of His32, Asp56, and Ser137, as shown below (with the catalytic triad indicated in bold and underline):

(SEQ ID NO: 2)
FDVIGGNAYT IGGRSRCSIG FAVNGGFITA GHCGRTGATT

ANPTGTFAGS SFPGNDYAFV RTGAGVNLLA QVNNYSGGRV

QVAGHTAAPV GSAVCRSGST TGWHCGTITA LNSSVTYPEG

TVRGLIRTTV CAEPGDSGGS LLAGNQAQGV TSGGSGNCRT

GGTTFFQPVN PILQAYGLRM ITTDSGSSP

Site evaluation libraries (SELs) were built as described herein by introducing from 12 to 19 substitutions at each of the 189 positions. The 2851 mutations at 189 positions were analyzed using three different activity assays and two different stability assays. There were on average 15 mutations per position.

Evaluation of SEL Variant Data

Table I provides the data for one position in the protein, namely position 14.

TABLE I

Performance Data for Position 14

| Position | Variant code | Casein activity ΔΔG | Keratin activity ΔΔG | AAPF activity ΔΔG | LAS stability ΔΔG | Thermal Stability ΔΔG |
|---|---|---|---|---|---|---|
| 14 | R014T | 0.35 | −0.11 | 0.05 | −0.86 | −0.05 |
| 14 | R014S | 0.28 | −0.07 | 0.13 | −0.63 | −0.05 |
| 14 | R014I | 0.15 | −0.19 | 0.21 | −0.53 | −0.05 |
| 14 | R014Q | 0.10 | −0.23 | 0.11 | −0.52 | −0.05 |
| 14 | R014N | 0.16 | −0.15 | 0.75 | −0.47 | −0.05 |
| 14 | R014H | 0.21 | −0.01 | 0.00 | −0.23 | −0.05 |
| 14 | R014K | 0.16 | −0.10 | −0.03 | 0.16 | −0.05 |
| 14 | R014R | 0 | 0 | 0 | 0 | 0 |
| 14 | R014W | 0.30 | −0.04 | −0.27 | 0.09 | 0.02 |
| 14 | R014G | 0.14 | −0.15 | 0.14 | −0.64 | 0.03 |
| 14 | R014L | 0.02 | −0.24 | −0.08 | −0.22 | 0.09 |
| 14 | R014E | −0.15 | −0.15 | −0.04 | −1.21 | 0.12 |
| 14 | R014D | 0.17 | −0.18 | 0.02 | −1.07 | 0.15 |
| 14 | R014P | 0.33 | −0.02 | 0.04 | −0.09 | 0.69 |
| 14 | R014M | 0.06 | −0.11 | 0.03 | −0.33 | 0.73 |
| 14 | R014A | 0.14 | −0.07 | 0.07 | −0.52 | 1.09 |
| 14 | R014C | 0.18 | 0.13 | 0.74 | −0.48 | 1.54 |

The wild type amino acid is listed as a reference point for every position. At position 14, R014R represents the wild type, and R014X represents each mutation measured. For each property, 16 measurements were used to determine the mean and standard deviation of $\Delta\Delta G_{app}$ for the parent enzyme. The parent mean ($\mu_{parent}$) was normalized to 0, and the standard deviation ($\sigma_{parent}$) for $\Delta\Delta G_{app}$ was determined. These values were used as the reference for each property at each position of the molecule, and in Table I are listed in the R014R line.

A summary of the results for all 2851 mutants is provided in Table II. The mutations were divided into two classes—"Up" and "Down." A mutant is "Up" if $\Delta\Delta G_{app}$ was negative or 0, and a mutant is "Down" if $\Delta\Delta G_{app}$ was positive. The probability that a mutation is Up or Down was determined by counting the number of mutations that were either Up or Down, and dividing this number by the total number of mutations (i.e., 2851 in the case of ASP). The probability that a mutation was Down (i.e., "pDown") for a particular property was found to range from 84-94%. The probability that a mutation was Up (i.e., "pUp") for a particular property was found to range from 6-16%. These data indicate that accumulating mutations that are good for one property requires that all other properties will get worse.

TABLE II

Summary of Results for Mutants

| | Casein activity ΔΔG | Keratin activity ΔΔG | AAPF activity ΔΔG | LAS stability ΔΔG | Thermal Stability ΔΔG |
|---|---|---|---|---|---|
| Up | 465 | 422 | 179 | 425 | 419 |
| Down | 2386 | 2429 | 2672 | 2426 | 2432 |
| Total | 2851 | 2851 | 2851 | 2851 | 2851 |
| p Up | 16% | 15% | 6% | 15% | 15% |
| p Down | 84% | 85% | 94% | 85% | 85% |

The distributions of the 2851 $\Delta\Delta G_{app}$ values obtained for each property are shown in FIG. 1. In some embodiments, the distribution for all properties is modeled as the sum of two or more Gaussian distributions. This is consistent with distributions of free energy for libraries reported in the literature (Lancet et al., Proc. Natl. Acad. Sci. USA 90:8367-8371 [1993]; and Lu et al., Proc. Natl. Acad. Sci. USA 98:1410-

1415 [2001]). Thus, the average $\Delta\Delta G_{app}$ values for each property were all substantially worse than the parent enzyme. For each mutant having 1% of the parent activity or less ($\Delta\Delta G_{app}$>2.7), the values were arbitrarily fixed at 1%, due to the error inherent in the assay systems. For each property, there were a substantial number of mutations that had 1% or less of the parent activity. Means and standard deviations were calculated for these data, and for the subset of mutants that exhibited more than 5% of the activity of the parent enzyme (See, Table III).

The mean $\Delta\Delta G_{app}$ values for each property for the 2851 variants varied from 0.9 to 1.5 Kcal/mole, which corresponded to 20% to 7% of the activity of the parent enzyme.

It is important to note that these distributions also represent the distributions of $\Delta\Delta G_{app}$ values that would be expected in random libraries that had on the average one mutation per member.

TABLE III

Mean and Standard Deviation for all Mutants

|  | CAS $\Delta\Delta G$ | KER $\Delta\Delta G$ | AAPF $\Delta\Delta G$ | LAS $\Delta\Delta G$ | THER $\Delta\Delta G$ |
| --- | --- | --- | --- | --- | --- |
| Mean and Standard Deviation for Mutants with ≤1% of the Parent Enzyme's Activity | | | | | |
| Mean | 1.01 | 0.93 | 1.45 | 1.52 | 1.36 |
| Std. Dev. | 1.10 | 1.00 | 1.11 | 1.25 | 1.21 |
| Mean and Standard Deviation for Mutants with >5% of the Parent Enzyme's Activity | | | | | |
| Mean | 0.31 | 0.46 | 0.52 | 0.33 | 0.37 |
| Std. Dev. | 0.47 | 0.56 | 0.49 | 0.63 | 0.52 |

The site evaluation data were tested for evidence of correlation between properties. The $\Delta\Delta G_{app}$ values for each property were plotted versus each other property and correlation coefficients were calculated and shown in Table IV. The two activity measurements on protein substrates were correlated ($r^2$=0.77), with only weak correlation ($r^2$=0.53) of either protein substrate with activity on the synthetic peptide substrate AAPF. Neither of the two stability measurements correlated with the activity measurements or with each other.

TABLE IV

Correlation Coefficients for Five Properties

|  | CAS | KER | AAPF | LAS | THER |
| --- | --- | --- | --- | --- | --- |
| CAS | 1 | | | | |
| KER | 0.77 | 1 | | | |
| AAPF | 0.53 | 0.53 | 1 | | |
| LAS | <0.01 | <0.01 | 0.13 | 1 | |
| THER | 0.01 | 0.01 | 0.06 | 0.24 | 1 |

Evaluation of SEL Position Data

In order to analyze the positions within the amino acid sequence, two types of sites were defined. "Unproductive" sites have no mutant that is better than the parent enzyme, while "Productive" sites have at least one substitution that is better than the parent enzyme. Table V provides the numbers of Productive and Unproductive sites for each property within ASP's 189 positions. The probability that a site will be Productive is given by the number of Productive sites divided by the total number of sites (189). Although the probability that any mutation will be better than the parent enzyme is low (i.e., 6%-28%) the probability that a given site will have at least one Up mutation is quite high.

TABLE V

Number and Percentage of Productive and Unproductive Sites in ASP

|  | Casein Act. $\Delta\Delta G$ | Keratin Act. $\Delta\Delta G$ | AAPF Act. $\Delta\Delta$ | LAS Stability $\Delta\Delta$ | Thermal Stability $\Delta\Delta$ |
| --- | --- | --- | --- | --- | --- |
| Unproductive | 82 | 92 | 144 | 86 | 59 |
| Productive | 107 | 97 | 45 | 103 | 130 |
| pUproductive | 43% | 49% | 76% | 46% | 31% |
| pProductive | 57% | 51% | 24% | 54% | 69% |

It was of interest to determine how the Productive and Unproductive sites were distributed with respect to structural features (e.g., buried amino acids, interacting amino acids, positions near the active site, etc.) in the ASP, as well as sequence sites that are conserved or changeable in evolution. To make this determination, the structure of ASP was examined and the sequence was aligned with 20 non-redundant homologs (Edgar, Nucl. Acids Res., 32:1792-1797 [2004]). The results are provided in Table VI.

TABLE VI

Analysis of Productive and Unproductive Sites

|  | CAS ratio | KER ratio | BMI ratio | LpH ratio | AAPF ratio | LAS ratio | THER ratio |
| --- | --- | --- | --- | --- | --- | --- | --- |
| Near Active Site | | | | | | | |
| Unproductive | 1.50 | 1.61 | 1.61 | 1.53 | 1.03 | 1.34 | 0.85 |
| Productive | 0.61 | 0.42 | 0.48 | 0.56 | 0.91 | 0.72 | 1.09 |
| Buried | | | | | | | |
| Unproductive | 1.65 | 1.66 | 1.71 | 1.62 | 1.31 | 1.67 | 1.39 |
| Productive | 0.50 | 0.37 | 0.40 | 0.48 | 0.00 | 0.44 | 0.78 |
| No Contacts | | | | | | | |
| Unproductive | 0.70 | 0.63 | 0.72 | 0.79 | 0.84 | 0.37 | 0.69 |
| Productive | 1.18 | 1.30 | 1.18 | 1.12 | 1.40 | 1.48 | 1.13 |
| More than 3 Contacts | | | | | | | |
| Unproductive | 1.67 | 1.49 | 1.57 | 1.52 | 1.27 | 1.36 | 1.44 |
| Productive | 0.49 | 0.54 | 0.51 | 0.57 | 0.14 | 0.70 | 0.75 |
| Conserved | | | | | | | |
| Unproductive | 2.23 | 2.05 | 2.10 | 2.13 | 1.27 | 1.91 | 1.34 |
| Productive | 0.06 | 0.00 | 0.06 | 0.06 | 0.14 | 0.24 | 0.81 |
| Variable | | | | | | | |
| Unproductive | 0.31 | 0.55 | 0.43 | 0.44 | 0.79 | 0.88 | 0.56 |
| Productive | 1.53 | 1.43 | 1.48 | 1.47 | 1.68 | 1.10 | 1.25 |
| Insertion or Deletion | | | | | | | |
| Unproductive | 0.34 | 0.53 | 0.40 | 0.81 | 0.88 | 0.81 | 0.82 |
| Productive | 1.50 | 1.52 | 1.51 | 1.22 | 1.56 | 1.22 | 1.04 |

It was remarkable that for the investigated properties, Productive sites were not found in the hydrophobic core of ASP. It is also interesting to note that none of the most productive sites for casein activity are in close proximity to the catalytic triad. Only one of the casein Productive (P118) sites has contact with the substrate. The rest of the casein productive sites are distributed over flexible surface loops all over the protein. None of the Productive sites for keratin activity are found near the active site. These sites were found to be spread over the surface of the whole molecule. The closest of the keratin productive sites is R014, which is still almost 13A away from the catalytic serine (S137, Ca-Ca distance).

The position of the LAS stability Productive sites follows the overall scheme of being spread over the flexible surface loops of the whole protein. This also applies for the location of the thermal stability Productive sites, with one exception: C033 has Vanderwaals contacts with and is consecutive neighbor of H032 in the amino acid sequence.

Based on the sequence alignment, sites were identified as being "conserved" (no differences in the 20 sequences), "variable" (6 or more different amino acids in the 20 sequences), or "sites of insertion or deletion" relative to ASP. The expected numbers were calculated from the probabilities that a site would meet the given conditions and be either Productive or Unproductive for a given property. The ratio of observed to expected numbers was calculated; numbers above 1.4 and below 0.6 were considered indicators of either over-representation or under-representation of a particular class of sites. The cutoff values were chosen based on results from ten randomly generated data sets that matched the numbers of each class of sites. It was found that buried residues and residues with several contacts are strongly correlated with Unproductive sites for protease activity on the two protein substrates, as well as stability to LAS. Surprisingly, positions near the active site were found to be more likely to be Unproductive than Productive. In the sequence alignment, sites that are conserved were especially likely to be Unproductive for activity on protein substrates and for LAS stability, while highly variable sites and sites of insertion or deletion were more likely to be Productive for activity, with little effect on stability.

As indicated in Example 5, deleterious mutations for any property are correlated with deleterious mutations for every other property, regardless of correlations of the properties. Only a small number of positions (5-10%) have mutations that are bad for all properties. These positions define the "fold" and are conserved in evolution. The implication of this is that although identification of beneficial mutations for any property requires a truly predictive screen for that property, identification of mutations likely to be deleterious for any property can be accomplished using ANY screen. A simplified protein engineering strategy is to build SELs and screen using a simple activity and/or stability screen. The deleterious mutations are identified and those positions that have few deleterious mutations are used to build libraries and combinatorial mutations to improve multiple properties. Also, picking sites that are on the surface of the protein, have few interactions and are variable in sequence alignments provides a high proportion of productive sites. Sites that are on the interior of the molecule, have many contacts and are strongly conserved in evolution will have a high probability of having deleterious mutations and should be avoided. It is contemplated that any suitable method for analyzing sequence and/or structural information will find use in the present invention, including but not limited to computer and/or electronic methods and/or programs.

The Tables provided in Example 5 provide pairwise comparisons of the numbers of variants with more than 5% wt activity and less than 5% activity for each of two properties, along with correlation coefficients for the two properties. The results from three enzymes, namely, ASP, ACT and NPRe, are shown, although it is not intended that the present invention be limited to these particular enzymes, as the methods provided herein find use with any protein.

The enzymes (ASP, ACT, and NPRe) and assay systems are described in detail in U.S. patent application Ser. Nos. 10/576,331 currently pending, 10/581,014 currently pending, 11/581,102 currently abandoned, and 11/583,334 currently abandoned, all of which are incorporated by reference in their entirety. In addition, the methods provided in U.S. Provisional Patent Application Ser. No. 60/933,312, filed Jun. 6, 2007, find use in conjunction with the present invention. The properties used herein were casein activity (CAS), keratin activity (KER), AAPF activity (AAPF), LAS stability (LAS) and thermal stability for ASP; and peracid fromation (PAF) and peracid degradation (PAD) for ACT. In these experiments, the only properties that were found to be correlated (correlation coefficients>0.5) were CAS, KER and AAPF for ASP. All of the others were not correlated (correlation coefficient<0.3). In spite of the fact that properties were not correlated, the probability that a mutation would be deleterious for the two properties is much higher than expected by chance. In the Table, the calculated ratios of observed numbers of variants expected based on chance are provided. Numbers that are greater than 1 indicate positive correlations, and numbers that are less than 1 indicate negative correlations.

Library Design

In some particularly preferred embodiments, the site evaluation library data are used for combinatorial library design. Traditional directed evolution builds random libraries and screens large numbers of library for single properties, combines these and repeats the process. As several investigators have found (See e.g., Bloom et al., Curr. Opin. Struct. Biol., 15:447-452 [2005]; Bloom et al., Proc. Natl. Acad. Sci. USA 103:5869-5874 [2006]; and Guo et al., Proc. Natl. Acad. Sci. USA 101:9205-9210 [2004]), the accumulation of positive mutations for one property commonly leads to decreases in other properties. This is also readily shown in Table II, since the probability that any mutation will be Up for any property is small, and the probability that any mutation will be Down is high (>85%), and the probability that accumulating more than three (3) mutations that increase activity will result in a decrease in several other properties is quite high.

However, this problem is avoided by using the site evaluation data to build libraries that would be good for multiple properties. Unproductive sites were not included in combinatorial libraries, and productive sites were further classified by the percentage of mutations that were Up. A group of four non-interacting sites (14-24-127-159) with high percentages of Up mutations for both LAS stability and keratin activity were used to design a library to improve both properties at once (See, Table VII).

TABLE VII

Percent of Variants That are Better Than the Parent Protein by Position

| Position | Wild-Type Amino Acid | Keratin ΔΔ (% Better) | LAS ΔΔ (% Better) |
|---|---|---|---|
| 14 | R | 94 | 88 |
| 24 | N | 67 | 40 |
| 127 | R | 63 | 69 |
| 159 | R | 83 | 78 |

Assuming additivity for the sites, predicted $\Delta\Delta G_{app}$ values were calculated for the library and compared to the values determined for the actual library. In some embodiments, for sites that are additive for the property the results typically agree. But, in other embodiments, in which the results do not agree with prediction, the way in which they disagree provides information about the interaction(s) of the sites, non-additivity of the properties, and/or the appropriateness of the assays used.

Figure 2A:
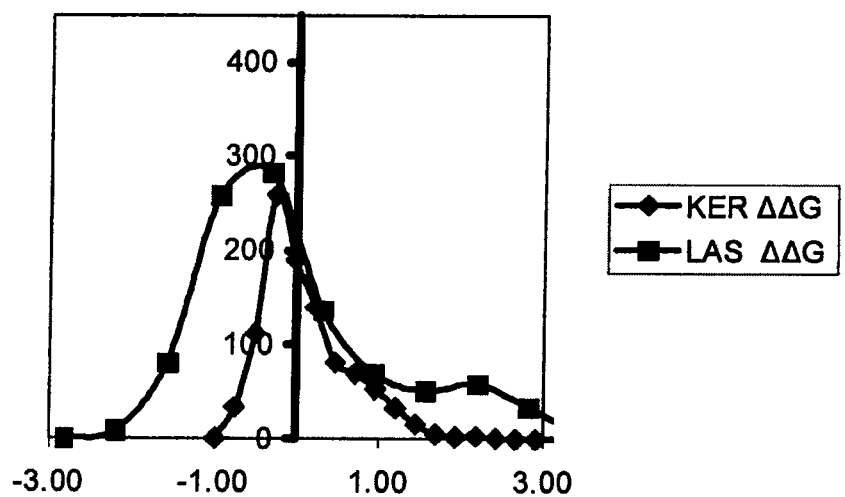
FIG. 2A provides results from calculating the expected distribution of values of $\Delta\Delta G_{app}$ for LAS stability and keratin activity for one thousand randomly chosen combinations of mutations at the four sites, as compared to the actual distribution of $\Delta\Delta G_{app}$ values for 64 randomly chosen members of the library.
Figure 2B:
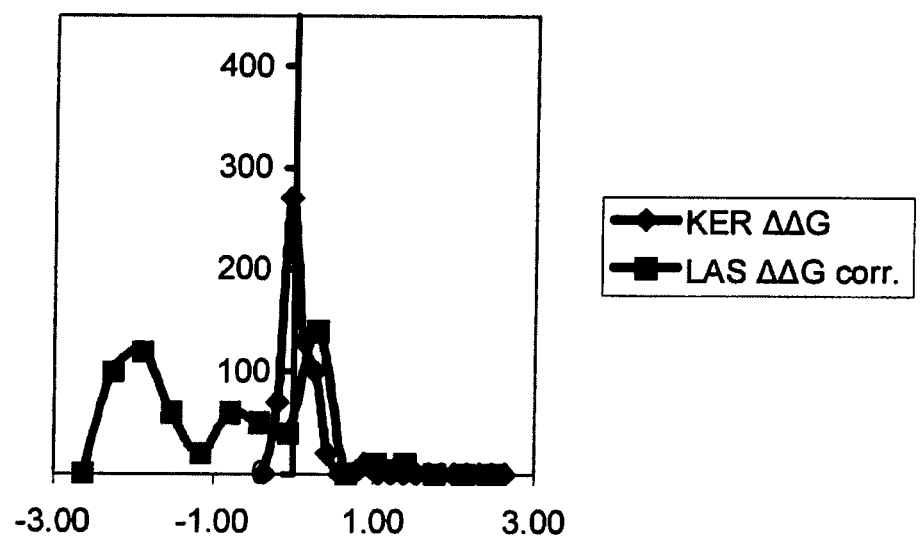
FIG. 2B shows the actual distribution observed for 64 randomly chosen members of the library.

The expected distribution of values of $\Delta\Delta G_{app}$ for LAS stability and keratin activity for one thousand randomly chosen combinations of mutations at the four sites were calculated and compared to the actual distribution of $\Delta\Delta G_{app}$ values for 64 randomly chosen members of the library. The results are shown in FIG. 2A. FIG. 2B shows the actual distribution observed for 64 randomly chosen members of the library. This library clearly has a large number of members that are better than the parent enzyme for both LAS stability and keratin activity. The observed mean for keratin activity of 0.02 Kcal agreed well with the predicted mean of −0.01 Kcal, consistent with additivity for these sites. For the LAS stability results, the observed mean of −1.13 significantly exceeded the expected value of −0.28, although the standard deviations were similar (See, Table VIII).

TABLE VIII

Observed Means and Standard Deviations for Keratin Activity and LAS Stability for Library 14-24-127-159

| | Property | |
|---|---|---|
| | Predicted | Observed |
| Keratin Activity | | |
| Mean | −0.01 | 0.02 |
| Std. Deviation | 0.53 | 0.39 |
| LAS Stability | | |
| Mean | −0.28 | −1.13 |
| Std. Deviation | 1.29 | 1.04 |

In the case of LAS stability, the original assay for the SEL mutants underestimated the true $\Delta\Delta G$ values. The assay was changed, with the temperature of incubation raised from 25° C. to 35° C., because most of the library members were stable under the assay conditions, and the library was assayed under harsher conditions. The $\Delta\Delta G_{app}$ values were corrected to account for this, but the correction probably still underestimated the true $\Delta\Delta G$ values, and the sites are probably still additive for LAS stability, given the agreement of the standard deviation.

Definitions

Unless otherwise indicated, the practice of the present invention involves conventional techniques commonly used in molecular biology, protein engineering, microbiology, and recombinant DNA, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the respective protease's ability to hydrolyze a commercial substrate. Exemplary substrates useful in the analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the terms "ASP protease," "Asp protease," and "Asp," refer to the serine proteases described herein. In some preferred embodiments, the Asp protease is the protease designed herein as 69B4 protease obtained from *Cellulomonas* strain 69B4. Thus, in preferred embodiments, the term "69B4 protease" refers to a naturally occurring mature protease derived from *Cellulomonas* strain 69B4 (DSM 16035) having substantially identical amino acid sequences as provided in SEQ ID NO:2. In alternative embodiments, the present invention provides portions of the ASP protease.

The term "*Cellulomonas* protease homologues" refers to naturally occurring proteases having substantially identical amino acid sequences to the mature protease derived from *Cellulomonas* strain 69B4 or polynucleotide sequences which encode for such naturally occurring proteases, and which proteases retain the functional characteristics of a serine protease encoded by such nucleic acids. In some embodiments, these protease homologues are referred to as "cellulomonadins."

As used herein, the terms "protease variant," "ASP variant," "ASP protease variant," and "69B protease variant" are used in reference to proteases that are similar to the wild-type ASP, particularly in their function, but have mutations in their amino acid sequence that make them different in sequence from the wild-type protease.

As used herein, "*Cellulomonas* ssp." refers to all of the species within the genus "*Cellulomonas*," which are Gram-positive bacteria classified as members of the Family Cellulomonadaceae, Suborder Micrococcineae, Order Actinomycetales, Class Actinobacteria. It is recognized that the genus *Cellulomonas* continues to undergo taxonomical reorganization. Thus, it is intended that the genus include species that have been reclassified.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

The terms "polynucleotide" and "nucleic acid", used interchangeably herein, refer to a polymeric form of nucleotides of any length, either ribonucleotides or deoxyribonucleotides. These terms include, but are not limited to, a single-, double-, or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In alternative embodiments, the sequence of nucleotides is interrupted by non-nucleotide components.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e. replace an endogenous sequence with a heterologous sequence), 3) delete target genes, and/or 4) introduce a replicating plasmid into the host.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, proteins are defined as having a common "fold" if they have the same major secondary structures in the same arrangement and with the same topological connections. Different proteins with the same fold often have peripheral elements of secondary structure and turn regions that differ in size and conformation. In some cases, these differing peripheral regions may comprise half the structure. Proteins placed together in the same fold category do not necessarily have a common evolutionary origin (e.g., structural similarities arising from the physics and chemistry of proteins favoring certain packing arrangements and chain topologies).

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene based on the *Cellulomonas* strain 69B4 protease. Additionally, analogous genes include at least 45%, 50%, 55%, 60%, 65%, 70%, 75%, 80%, 85%, 90%, 95%, 97%, 98%, 99% or 100% sequence identity with the sequence of the *Cellulomonas* strain 69B4 protease. Alternately, analogous sequences have an alignment of between 70 to 100% of the genes found in the *Cellulomonas* strain 69B4 protease region and/or have at least between 5-10 genes found in the region aligned with the genes in the *Cellulomonas* strain 69B4 chromosome. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

"Homologous recombination" means the exchange of DNA fragments between two DNA molecules or paired chromosomes at the site of identical or nearly identical nucleotide sequences. In a preferred embodiment, Chromosomal integration is homologous recombination.

As used herein "amino acid" refers to peptide or protein sequences or portions thereof. The terms "protein," "peptide," and "polypeptide" are used interchangeably.

As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In particularly preferred embodiments, these enzyme include the serine proteases of the present invention. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences. As is known in the art, a DNA can be transcribed by an RNA polymerase to produce RNA, but an RNA can be reverse transcribed by reverse transcriptase to produce a DNA. Thus a DNA can encode a RNA and vice versa.

"Host strain" or "host cell" refers to a suitable host for an expression vector comprising DNA according to the present invention.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

A "prosequence" is an amino acid sequence between the signal sequence and mature protease that is necessary for the secretion of the protease. Cleavage of the pro sequence results in a mature active protease.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536).

The term "hybrid signal sequence" refers to signal sequences in which part of sequence is obtained from the expression host fused to the signal sequence of the gene to be expressed. In some embodiments, synthetic sequences are utilized.

The term "mature" form of a protein or peptide refers to the final functional form of the protein or peptide. For example, a mature form of the protease of the present invention includes at least the amino acid sequence identical to residue positions 1-189 of SEQ ID NO:2.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from *Cellulomonas*" refers to those enzymes having proteolytic activity which are naturally-produced by *Cellulomonas*, as well as to serine proteases like those produced by *Cellulomonas* sources but which through the use of genetic engineering techniques are produced by non-*Cellulomonas* organisms transformed with a nucleic acid encoding said serine proteases.

A "derivative" within the scope of this definition generally retains the characteristic proteolytic activity observed in the wild-type, native or parent form to the extent that the derivative is useful for similar purposes as the wild-type, native or parent form. Functional derivatives of serine protease encompass naturally occurring, synthetically or recombinantly produced peptides or peptide fragments which have the general characteristics of the serine protease of the present invention.

The term "functional derivative" refers to a derivative of a nucleic acid which has the functional characteristics of a nucleic acid which encodes serine protease. Functional derivatives of a nucleic acid which encode serine protease of the present invention encompass naturally occurring, synthetically or recombinantly produced nucleic acids or fragments and encode serine protease characteristic of the present invention. Wild type nucleic acid encoding serine proteases according to the invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucloetide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The phrase "equivalent," in this context, refers to serine proteases enzymes that are encoded by a polynucleotide capable of hybridizing to the polynucleotide having the sequence as shown in SEQ ID NO:1, under conditions of medium to maximum stringency. For example, being equivalent means that an equivalent mature serine protease comprises at least 70%, at least 75%, at least 80%, at least 85%, at least 90%, at least 91%, at least 92%, at least 93%, at least 94%, at least 95%, at least 96%, at least 97%, at least 98% and/or at least 99% sequence identity to the mature Cellulomonas serine protease having the amino acid sequence of SEQ ID NO:2.

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78 [1985]). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than 10% pure, preferably more than 20% pure, and even more preferably more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations which were not members of the predefined set of mutations. In some embodiments, the methods include those set forth in U.S. patent application Ser. No. 09/699,250, filed Oct. 26, 2000, hereby incorporated by reference. In alternative embodiments, combinatorial mutagenesis methods encompass commercially available kits (e.g., QuikChange® Multisite, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein, the term "starting gene" refers to a gene of interest that encodes a protein of interest that is to be improved and/or changed using the present invention.

As used herein, the term "multiple sequence alignment" ("MSA") refers to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence resulting from an MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "initial hit" refers to a variant that was identified by screening a combinatorial consensus mutagenesis library. In preferred embodiments, initial hits have improved performance characteristics, as compared to the starting gene.

As used herein, the term "improved hit" refers to a variant that was identified by screening an enhanced combinatorial consensus mutagenesis library.

As used herein, the terms "improving mutation" and "performance-enhancing mutation" refer to a mutation that leads to improved performance when it is introduced into the starting gene. In some preferred embodiments, these mutations are identified by sequencing hits that were identified during the screening step of the method. In most embodiments, mutations that are more frequently found in hits are likely to be improving mutations, as compared to an unscreened combinatorial consensus mutagenesis library.

As used herein, the term "enhanced combinatorial consensus mutagenesis library" refers to a CCM library that is designed and constructed based on screening and/or sequencing results from an earlier round of CCM mutagenesis and screening. In some embodiments, the enhanced CCM library is based on the sequence of an initial hit resulting from an earlier round of CCM. In additional embodiments, the enhanced CCM is designed such that mutations that were frequently observed in initial hits from earlier rounds of mutagenesis and screening are favored. In some preferred embodiments, this is accomplished by omitting primers that encode performance-reducing mutations or by increasing the concentration of primers that encode performance-enhancing mutations relative to other primers that were used in earlier CCM libraries.

As used herein, the term "performance-reducing mutations" refer to mutations in the combinatorial consensus mutagenesis library that are less frequently found in hits resulting from screening as compared to an unscreened combinatorial consensus mutagenesis library. In preferred embodiments, the screening process removes and/or reduces the abundance of variants that contain "performance-reducing mutations."

As used herein, the term "functional assay" refers to an assay that provides an indication of a protein's activity. In particularly preferred embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some preferred embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $K_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc.

As used herein, the term "screening" has its usual meaning in the art and is, in general a multi-step process. In the first step, a mutant nucleic acid or variant polypeptide therefrom is provided. In the second step, a property of the mutant nucleic acid or variant polypeptide is determined. In the third step, the determined property is compared to a property of the corresponding precursor nucleic acid, to the property of the corresponding naturally occurring polypeptide or to the property of the starting material (e.g., the initial sequence) for the generation of the mutant nucleic acid.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, screens encompass selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In a preferred embodiment, a library of variants is exposed to stress (heat, protease, denaturation) and subsequently variants that are still intact are identified in a screen or enriched by selection. It is intended that the term encompass any suitable means for selection. Indeed, it is not intended that the present invention be limited to any particular method of screening.

As used herein, the term "targeted randomization" refers to a process that produces a plurality of sequences where one or several positions have been randomized. In some embodiments, randomization is complete (i.e., all four nucleotides, A, T, G, and C can occur at a randomized position. In alternative embodiments, randomization of a nucleotide is limited to a subset of the four nucleotides. Targeted randomization can be applied to one or several codons of a sequence, coding for one or several proteins of interest. When expressed, the resulting libraries produce protein populations in which one or more amino acid positions can contain a mixture of all 20 amino acids or a subset of amino acids, as determined by the randomization scheme of the randomized codon. In some embodiments, the individual members of a population resulting from targeted randomization differ in the number of amino acids, due to targeted or random insertion or deletion of codons. In further embodiments, synthetic amino acids are included in the protein populations produced. In some preferred embodiments, the majority of members of a population resulting from targeted randomization show greater sequence homology to the consensus sequence than the starting gene. In some embodiments, the sequence encodes one or more proteins of interest. In alternative embodiments, the proteins have differing biological functions. In some preferred embodiments, the incoming sequence comprises at least one selectable marker. This sequence can code for one or more proteins of interest. It can have other biological function. In many cases the incoming sequence will include a selectable marker, such as a gene that confers resistance to an antibiotic.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions which will match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 15-45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added. Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

As used herein, the phrase "contiguous mutations" refers to mutations which are presented within the same oligonucleotide primer. For example, contiguous mutations may be adjacent or nearby each other, however, they will be introduced into the resulting mutant template nucleic acids by the same primer.

As used herein, the phrase "discontiguous mutations" refers to mutations which are presented in separate oligonucleotide primers. For example, discontiguous mutations will be introduced into the resulting mutant template nucleic acids by separately prepared oligonucleotide primers.

The terms "wild-type sequence," or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention.

As used herein, the term "antibodies" refers to immunoglobulins. Antibodies include but are not limited to immunoglobulins obtained directly from any species from which it is desirable to produce antibodies. In addition, the present invention encompasses modified antibodies. The term also refers to antibody fragments that retain the ability to bind to the epitope that the intact antibody binds and include polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), light chain variable region (VL). Polyclonal and monoclonal antibodies are also encompassed by the present invention. Preferably, the antibodies are monoclonal antibodies.

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least 50%, 60%, 70%, 75%, 80%, 85%, 90%, 92%, 95%, 96%, 97%, 98% or 99% proteolytic activity after contact with a bleaching or oxidizing agent over a given time period, for example, at least 1 minute, 3 minutes, 5 minutes, 8 minutes, 12 minutes, 16 minutes, 20 minutes, etc. In some embodiments, the stability is measured as described in the Examples.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least 50%, 60%, 70%, 75%, 80%, 85%, 90%, 92%, 95%, 96%, 97%, 98% or 99% proteolytic activity after contact with a chelating agent over a given time period, for example, at least 10 minutes, 20 minutes, 40 minutes, 60 minutes, 100 minutes, etc. In some embodiments, the chelator stability is measured as described in the Examples.

The terms "thermally stable" and "thermostable" refer to proteases of the present invention that retain a specified amount of enzymatic activity after exposure to identified temperatures over a given period of time under conditions prevailing during the proteolytic, hydrolyzing, cleaning or other process of the invention, for example while exposed altered temperatures. Altered temperatures includes increased or decreased temperatures. In some embodiments, the proteases retain at least 50%, 60%, 70%, 75%, 80%, 85%, 90%, 92%, 95%, 96%, 97%, 98% or 99% proteolytic activity after exposure to altered temperatures over a given time period, for example, at least 60 minutes, 120 minutes, 180 minutes, 240 minutes, 300 minutes, etc. In some embodiments, the thermostability is determined as described in the Examples.

The term "enhanced stability" in the context of an oxidation, chelator, thermal and/or pH stable protease refers to a higher retained proteolytic activity over time as compared to other serine proteases (e.g., subtilisin proteases) and/or wild-type enzymes.

The term "diminished stability" in the context of an oxidation, chelator, thermal and/or pH stable protease refers to a lower retained proteolytic activity over time as compared to other serine proteases (e.g., subtilisin proteases) and/or wild-type enzymes.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, bar) composition is required, etc.

The term "cleaning adjunct materials," as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

The term "enhanced performance" in the context of cleaning activity refers to an increased or greater cleaning activity of certain enzyme sensitive stains such as egg, milk, grass or blood, as determined by usual evaluation after a standard wash cycle and/or multiple wash cycles.

The term "diminished performance" in the context of cleaning activity refers to an decreased or lesser cleaning activity of certain enzyme sensitive stains such as egg, milk, grass or blood, as determined by usual evaluation after a standard wash cycle.

The term "comparative performance" in the context of cleaning activity refers to at least 60%, at least 70%, at least 80% at least 90% at least 95% of the cleaning activity of a comparative subtilisin protease (e.g., commercially available proteases), including but not limited to OPTIMASE™ protease (Genencor), PURAFECT™ protease products (Genencor), SAVINASE™ protease (Novozymes), BPN'-variants (See e.g., U.S. Pat. No. Re 34,606), RELASE™, DURAZYME™, EVERLASE™, KANNASE™ protease (Novozymes), MAXACAL™, MAXAPEM™, PROPERASE™ proteases (Genencor; See also, U.S. Pat. No. Re 34,606, and U.S. Pat. Nos. 5,700,676; 5,955,340; 6,312,936; and 6,482,628), and *B. lentus* variant protease products (e.g., those described in WO 92/21760, WO 95/23221 and/or WO 97/07770). Exemplary subtilisin protease variants include, but are not limited to those having substitutions or deletions at residue positions equivalent to positions 76, 101, 103, 104, 120, 159, 167, 170, 194, 195, 217, 232, 235, 236, 245, 248, and/or 252 of BPN'. Cleaning performance can be determined by comparing the proteases of the present invention with those subtilisin proteases in various cleaning assays concerning enzyme sensitive stains such as grass, blood or milk as determined by usual spectrophotometric or analytical methodologies after standard wash cycle conditions.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically 17-35% by weight of the total composition. In contrast, in compact compositions, the filler salt is present in amounts not exceeding 15% of the total composition. In some embodiments, the filler salt is present in amounts that do not exceed 10%, or more preferably, 5%, by weight of the composition. In some embodiments, the inorganic filler salts are selected from the alkali and alkaline-earth-metal salts of sulfates and chlorides. A preferred filler salt is sodium sulfate.

EXPERIMENTAL

The present invention is described in further detail in the following Examples which are not in any way intended to limit the scope of the invention as claimed. The attached Figures are meant to be considered as integral parts of the specification and description of the invention. All references cited are herein specifically incorporated by reference for all that is described therein. The following Examples are offered to illustrate, but not to limit the claimed invention In the experimental disclosure which follows, the following abbreviations apply: PI (proteinase inhibitor), ppm (parts per million); M (molar); mM (millimolar); µM (micromolar); nM (nanomolar); mol (moles); mmol (millimoles); µmol (micromoles); nmol (nanomoles); gm (grams); mg (milligrams);

gig (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); SOC (2% Bacto-Tryptone, 0.5% Bacto Yeast Extract. 10 mM NaCl, 2.5 mM KCl); Terrific Broth (TB; 12 g/l Bacto Tryptone, 24 g/l glycerol. 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN® 20); PEG (polyethylene glycol); PCR (polymerase chain reaction); RT-PCR (reverse transcription PCR); SDS (sodium dodecyl sulfate); Tris (tris(hydroxymethyl)aminomethane); HEPES (N-[2-Hydroxyethyl]piperazine-N-[2-ethanesulfonic acid]); HBS (HEPES buffered saline); Tris-HCl (tris[Hydroxymethyl] aminomethane-hydrochloride); Tricine (N-[tris-(hydroxymethyl)-methyl]-glycine); CHES (2-(N-cyclo-hexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); μCi (microCuries); HPLC (high pressure liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); EGTA (ethylene glycol-bis(β-aminoethyl ether) N,N,N',N'-tetraacetic acid); EDTA (ethylenediaminetetracetic acid); bla (β-lactamase or ampicillin-resistance gene); HDL (high density liquid); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y.); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, the Netherlands); Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Enichem (Enichem Iberica, Barcelona. Spain); Fluka Chemie AG (Fluka Chemie AG, Buchs, Switzerland); Gist-Brocades (Gist-Brocades, Nev., Delft, the Netherlands); Dow Corning (Dow Corning Corp., Midland. MI); and Microsoft (Microsoft, Inc., Redmond, Wash.).

The wild-type serine protease used in the following Examples is described in detail in US04/39006 and US04/39066, both of which are herein incorporated by reference in their entirety.

Example 1

Assays

In the following Examples, various assays were used, such as protein determinations, application-based tests, and stability-based tests. For ease in reading, the following assays are set forth below and referred to in the respective Examples. Any deviations from the protocols provided below in any of the experiments performed during the development of the present invention are indicated in the Examples.

A. TCA Assay for Protein Content Determination in 96-Well Microtiter Plates

This assay was started using filtered culture supernatant from microtiter plates grown 4 days at 33° C. with shaking at 230 RPM and humidified aeration. A fresh 96-well flat bottom plate was used for the assay. First, 100 µL/well of 0.25 N HCl were placed in the wells. Then, 50 µL filtered culture broth were added to the wells. The light scattering/absorbance at 405 nm (use 5 sec mixing mode in the plate reader) was then determined, in order to provide the "blank" reading.

For the test, 100 µL/well 15% (w/v) TCA was placed in the plates and incubated between 5 and 30 min at room temperature. The light scattering/absorbance at 405 nm (use 5 sec mixing mode in the plate reader) was then determined.

The calculations were performed by subtracting the blank (i.e., no TCA) from the test reading with TCA. If desired, a standard curve can be created by calibrating the TCA readings with AAPF assays of clones with known conversion factors. However, the TCA results are linear with respect to protein concentration from 50 to 500 ppm and can thus be plotted directly against enzyme performance for the purpose of choosing good-performing variants.

B. suc-AAPF-pNA Assay of Proteases in 96-Well Microtiter Plates

In this assay system, the reagent solutions used were:
1. 100 mM Tris/HCl, pH 8.6, containing 0.005% TWEEN®-80 (Tris buffer)
2. 100 mM Tris buffer, pH 8.6, containing 10 mM $CaCl_2$ and 0.005% TWEEN®-80 (Tris buffer)
3. 160 mM suc-AAPF-pNA in DMSO (suc-AAPF-pNA stock solution) (Sigma: S-7388)

To prepare suc-AAPF-pNA working solution, 1 ml AAPF stock was added to 100 ml Tris buffer and mixed well for at least 10 seconds.

The assay was performed by adding 10 µl of diluted protease solution to each well, followed by the addition (quickly) of 190 µl 1 mg/ml AAPF-working solution. The solutions were mixed for 5 sec., and the absorbance change was read at 410 nm in an MTP reader, at 25° C. The protease activity was expressed as AU (activity=$\Delta OD \cdot min^{-1} \cdot ml^{-1}$).

C. Keratin Hydrolysis Assay

In this assay system, the chemical and reagent solutions used were:

| | |
|---|---|
| Keratin | ICN 902111 |
| Detergent | 1.6 g. detergent was dissolved in 1000 ml water (pH = 8.2) 0.6 ml. CaCl2/MgCl2 of 10,000 gpg was also added, as well 1190 mg HEPES, giving a hardness and buffer strength of 6 gpg and 5 mM respectively. The pH was adjusted to 8.2 with NaOH. Picrylsulfonic acid (TNBS) Sigma P-2297 (5% solution in water) |
| Reagent A | 45.4 g $Na_2B_4O_7$•10H2O (Merck 6308) and 15 ml of 4N NaOH were dissolved together to a final volume of 1000 ml (by heating if needed) |
| Reagent B | 35.2 g $NaH_2PO_4$•1$H_2O$ (Merck 6346) and 0.6 g $Na_2SO_3$ (Merck 6657) were dissolved together to a final volume of 1000 ml. |

Method:

Prior to the incubations, keratin was sieved on a 100 µm sieve in small portions at a time. Then, 10 g of the <100 µm keratin was stirred in detergent solution for at least 20 minutes at room temperature with regular adjustment of the pH to 8.2.

Finally, the suspension was centrifuged for 20 minutes at room temperature (Sorvall, GSA rotor, 13,000 rpm). This procedure was then repeated. Finally, the wet sediment was suspended in detergent to a total volume of 200 ml., and the suspension was kept stirred during pipetting. Prior to incubation, microtiter plates (MTPs) were filled with 200 µl substrate per well with a Biohit multichannel pipette and 1200 µl tip (6 dispenses of 200 µl and dispensed as fast as possible to avoid settling of keratin in the tips). Then, 10 µl of the filtered culture was added to the substrate containing MTPs. The plates were covered with tape, placed in an incubator and incubated at 20° C. for 3 hours at 350 rpm (Innova 4330 [New Brunswick]). Following incubation, the plates were centrifuged for 3 minutes at 3000 rpm (Sigma 6K 15 centrifuge). About 15 minutes before removal of the 1" plate from the incubator, the TNBS reagent was prepared by mixing 1 ml TNBS solution per 50 ml of reagent A.

MTPs were filled with 60 µl TNBS reagent A per well. From the incubated plates, 10 µl was transferred to the MTPs with TNBS reagent A. The plates were covered with tape and shaken for 20 minutes in a bench shaker (BMG Thermostar) at room temperature and 500 rpm. Finally, 200 µl of reagent B was added to the wells, mixed for 1 minute on a shaker, and the absorbance at 405 nm was measured with the MTP-reader.

Calculation of the Keratin Hydrolyzing Activity

The obtained absorbance value was corrected for the blank value (substrate without enzyme). The resulting absorbance provides a measure for the hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme. A performance index (PI) that is greater than 1 (PI>1) identifies a better variant (as compared to the standard [e.g., wild-type]), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

D. Dimethylcasein Hydrolysis Assay (96 Wells)

In this assay system, the chemical and reagent solutions used were:

Dimethylcasein (DMC): Sigma C-9801

TWEEN®-80: Sigma P-8074

PIPES buffer (free acid): Sigma P-1851; 15.1 g is dissolved in about 960 ml water; pH is adjusted: to 7.0 with 4N NaOH, 1 ml 5% TWEEN®-80 is added and the volume brought up to 1000 ml. The final concentration of PIPES and TWEEN®-80 is 50 mM and 0.005% respectively.

Picrylsulfonic acid (TNBS): Sigma P-2297 (5% solution in water)

Reagent A: 45.4 g $Na_2B_4O_7$.10H2O (Merck 6308) and 15 ml of 4N NaOH are dissolved together to a final volume of 1000 ml (by heating if needed)

Reagent B: 35.2 g $NaH_2PO_4$.1$H_2O$ (Merck 6346) and 0.6 g $Na_2SO_3$ (Merck 6657) are dissolved together to a final volume of 1000 ml.

Method:

To prepare the substrate, 4 g DMC were dissolved in 400 ml PIPES buffer. The filtered culture supernatants were diluted with PIPES buffer; the final concentration of the controls in the growth plate was 20 ppm. Then, 10 µl of each diluted supernatant were added to 200 µl substrate in the wells of a MTP. The MTP plate was covered with tape, shaken for a few seconds and placed in an oven at 37° C. for 2 hours without agitation.

About 15 minutes before removal of the $1^{st}$ plate from the oven, the TNBS reagent was prepared by mixing 1 ml TNBS solution per 50 ml of reagent A. MTPs were filled with 60 µl TNBS reagent A per well. The incubated plates were shaken for a few seconds, after which 10 µl were transferred to the MTPs with TNBS reagent A. The plates were covered with tape and shaken for 20 minutes in a bench shaker (BMG Thermostar) at room temperature and 500 rpm. Finally, 200 µl reagent B were added to the wells, mixed for 1 minute on a shaker, and the absorbance at 405 nm was determined using an MTP-reader.

Calculation of Dimethylcasein Hydrolyzing Activity:

The obtained absorbance value was corrected for the blank value (substrate without enzyme). The resulting absorbance is a measure for the hydrolytic activity. The (arbitrary) specific activity of a sample was calculated by dividing the absorbance and the determined protein concentration.

E. Thermostability Assay

This assay is based on the dimethylcasein hydrolysis, before and after heating of the buffered culture supernatant. The same chemical and reagent solutions were used as described in the dimethylcasein hydrolysis assay.

Method:

The filtered culture supernatants were diluted to 20 ppm in PIPES buffer (based on the concentration of the controls in the growth plates). Then, 50 µl of each diluted supernatant were placed in the empty wells of a MTP. The MTP plate was incubated in an iEMS incubator/shaker HT (Thermo Labsystems) for 90 minutes at 60° C. and 400 rpm. The plates were cooled on ice for 5 minutes. Then, 10 µl of the solution was added to a fresh MTP containing 200 µl dimethylcasein substrate/well. This MTP was covered with tape, shaken for a few seconds and placed in an oven at 37° C. for 2 hours without agitation. The same detection method as used for the DMC hydrolysis assay was used.

Calculation of Thermostability:

The residual activity of a sample was expressed as the ratio of the final absorbance and the initial absorbance, both corrected for blanks.

F. LAS Stability Assay

LAS stability was measured after incubation of the test protease in the presence of 0.06% LAS (dodecylbenzenesulfonate sodium), and the residual activity was determined using the AAPF assay.

Reagents:
Dodecylbenzenesulfonate, Sodium salt (=LAS): Sigma D-2525
TWEEN®-80: Sigma P-8074
TRIS buffer (free acid): Sigma T-1378); 6.35 g is dissolved in about 960 ml water; pH is adjusted to 8.2 with 4N HCl. Final concentration of TRIS is 52.5 mM.
LAS stock solution: Prepare a 10.5% LAS solution in MQ water (=10.5 g per 100 ml MQ)
TRIS buffer-100 mM/pH 8.6 (100 mM Tris/0.005% Tween80)
TRIS-Ca buffer, pH 8.6 (100 mM Tris/10 mM CaCl2/0.005% Tween80)

Hardware:
Flat bottom MTPs: Costar (#9017)
Biomek FX
ASYS Multipipettor
Spectramax MTP Reader
iEMS Incubator/Shaker
Innova 4330 Incubator/Shaker
Biohit multichannel pipette
BMG Thermostar Shaker Method:

A 0.063% LAS solution was prepared in 52.5 mM Tris buffer pH 8.2. The AAPF working solution was prepared by adding 1 ml of 100 mg/ml AAPF stock solution (in DMSO) to 100 ml (100 mM) TRIS buffer, pH 8.6. To dilute the supernatants, flat-bottomed plates were filled with dilution buffer and an aliquot of the supernatant was added and mixed well. The dilution ratio depended on the concentration of the ASP-controls in the growth plates (AAPF activity). The desired protein concentration was 80 ppm.

Ten µl of the diluted supernatant were added to 190 µl 0.063% LAS buffer/well. The MTP was covered with tape, shaken for a few seconds and placed in an incubator (Innova 4230) at 25° or 35° C., for 60 minutes at 200 rpm agitation. The initial activity (t=10 minutes) was determined after 10 minutes of incubation by transferring 10 µl of the mixture in each well to a fresh MTP containing 190 µl AAPF work solution. These solutions were mixed well and the AAPF activity was measured using a MTP Reader (20 readings in 5 minutes and 25° C.).

The final activity (t=60 minutes) was determined by removing another 10 µl of solution from the incubating plate after 60 minutes of incubation. The AAPF activity was then determined as described above. The calculations were performed as follows: the % Residual Activity was [t−60 value] *100/[t−10 value].

Example 2

Production of 69B4 Protease from the Gram-Positive Alkaliphilic Bacterium 69B4

This Example provides a description of the *Cellulomonas* strain 69B4 used to initially isolate the novel protease 69B4 provided by the present invention. The alkaliphilic microorganism *Cellulomonas* strain 69B.4, (DSM 16035) was isolated at 37° C. on an alkaline casein medium containing (g $L^{-1}$) (See e.g., Duckworth et al., FEMS Microbiol. Ecol., 19:181-191 [1996]).

| | |
|---|---|
| Glucose (Merck 1.08342) | 10 |
| Peptone (Difco 0118) | 5 |
| Yeast extract (Difco 0127) | 5 |
| $K_2HPO_4$ | 1 |
| $MgSO_4 \cdot 7H_2O$ | 0.2 |
| NaCl | 40 |
| $Na_2CO_3$ | 10 |
| Casein | 20 |
| Agar | 20 |

An additional alkaline cultivation medium (Grant Alkaliphile Medium) was also used to cultivate *Cellulomonas* strain 69B.4, as provided below:

Grant Alkaliphile Medium ("GAM") Solution A (g $L^{-1}$)

| | |
|---|---|
| Glucose (Merck 1.08342) | 10 |
| Peptone (Difco 0118) | 5 |
| Yeast extract (Difco 0127) | 5 |
| $K_2HPO_4$ | 1 |
| $MgSO_4 \cdot 7H_2O$ | 0.2 |

Dissolved in 800 ml distilled water and sterilized by autoclaving

GAM Solution B (g L$^1$)

| | |
|---|---|
| NaCl | 40 |
| Na$_2$CO$_3$ | 10 |

Dissolved in 200 ml distilled water and sterilized by autoclaving.

Complete GAM medium was prepared by mixing Solution A (800 ml) with Solution B (200 ml). Solid medium is prepared by the addition of agar (2% w/v).

Growth Conditions

From a freshly thawed glycerol vial of culture (stored as a frozen glycerol (20% v/v, stock stored at −80° C.), the microorganisms were inoculated using an inoculation loop on Grant Alkaliphile Medium (GAM) described above in agar plates and grown for at least 2 days at 37° C. One colony was then used to inoculate a 500 ml shake flask containing 100 ml of GAM at pH 10. This flask was then incubated at 37° C. in a rotary shaker at 280 rpm for 1-2 days until good growth (according to visual observation) was obtained. Then, 100 ml of broth culture was subsequently used to inoculate a 7 L fermentor containing 5 liters of GAM. The fermentations were run at 37° C. for 2-3 days in order to obtain maximal production of protease. Fully aerobic conditions were maintained throughout by injecting air, at a rate of 5 L/min, into the region of the impeller, which was rotating at about 500 rpm. The pH was set at pH 10 at the start, but was not controlled during the fermentation.

Preparation of 69B4 Crude Enzyme Samples

Culture broth was collected from the fermentor, and cells were removed by centrifugation for 30 min at 5000×g at 10° C. The resulting supernatant was clarified by depth filtration over Seitz EKS (SeitzSchenk Filtersystems). The resulting sterile culture supernatant was further concentrated approximately 10 times by ultra filtration using an ultrafiltration cassette with a 10 kDa cut-off (Pall Omega 10 kDa Minisette; Pall). The resulting concentrated crude 69B4 samples were frozen and stored at −20° C. until further use.

Purification

The cell separated culture broth was dialyzed against 20 mM (2-(4-morpholino)-ethane sulfonic acid ("MES"), pH 5.4, 1 mM CaCl$_2$ using 8K Molecular Weight Cut Off (MWCO) Spectra-Por7 (Spectrum) dialysis tubing. The dialysis was performed overnight or until the conductivity of the sample was less than or equal to the conductivity of the MES buffer. The dialyzed enzyme sample was purified using a BioCad VISION (Applied Biosystems) with a 10×100 mm (7.845 mL) POROS High Density Sulfo-propyl (HS) 20 (20 micron) cation-exchange column (PerSeptive Biosystems). After loading the enzyme on the previously equilibrated column at 5 mL/min, the column was washed at 40 mL/min with a pH gradient from 25 mM MES, pH 6.2, 1 mM CaCl$_2$ to 25 mM (N-[2-hydroxyethyl]piperazine-N'-[2-ethane]sulfonic acid [C$_8$H$_{18}$N$_2$O$_4$S, CAS #7365-45-9]) ("HEPES") pH 8.0, 1 mM CaCl$_2$ in 25 column volumes. Fractions (8 mL) were collected across the run. The pH 8.0 wash step was held for 5 column volumes and then the enzyme was eluted using a gradient (0-100 mM NaCl in the same buffer in 35 column volumes). Protease activity in the fractions was monitored using the pNA assay (sAAPF-pNA assay; DelMar, et al., supra). Protease activity which eluted at 40 mM NaCl was concentrated and buffer exchanged (using a 5K MWCO VIVA Science 20 mL concentrator) into 20 mM MES, pH 5.8, 1 mMCaCl2. This material was used for further characterization of the enzyme.

Example 3

ASP Protease Production in *B. subtilis*

Experiments conducted to produce 69B4 protease (also referred to herein as "ASP," "Asp," and "ASP protease," and "Asp protease") in *B. subtilis* are described in U.S. patent application Ser. No. 10/576,331, incorporated herein by reference in its entirety.

The DNA sequence (synthetic ASP DNA sequence) is provided below, with codon usage adapted for *Bacillus* species, encodes the wild type ASP precursor protein:

(SEQ ID NO: 1)
ATGACACCACGAACTGTCACAAGAGCTCTGGCTGTGGCAACAGCAGCT

GCTACACTCTTGGCTGGGGGTATGGCAGCACAAGCTAACGAACCGGCT

CCTCCAGGATCTGCATCAGCCCCTCCACGATTAGCTGAAAAACTTGAC

CCTGACTTACTTGAAGCAATGGAACGCGATCTGGGGTTAGATGCAGAG

GAAGCAGCTGCAACGTTAGCTTTTCAGCATGACGCAGCTGAAACGGGA

GAGGCTCTTGCTGAGGAACTCGACGAAGATTTCGCGGGCACGTGGGTT

GAAGATGATGTGCTGTATGTTGCAACCACTGATGAAGATGCTGTTGAA

GAAGTCGAAGGCGAAGGAGCAACTGCTGTGACTGTTGAGCATTCTCTT

GCTGATTTAGAGGCGTGGAAGACGGTTTTGGATGCTGCGCTGGAGGGT

CATGATGATGTGCCTACGTGGTACGTCGACGTGCCTACGAATTCGGTA

GTCGTTGCTGTAAAGGCAGGAGCGCAGGATGTAGCTGCAGGACTTGTG

GAAGGCGCTGATGTGCCATCAGATGCGGTCACTTTTGTAGAAACGGAC

GAAACGCCTAGAACGATGTTCGACGTAATTGGAGGCAACGCATATACT

ATTGGCGGCCGGTCTAGATGTTCTATCGGATTCGCAGTAAACGGTGGC

TTCATTACTGCCGGTCACTGCGGAAGAACAGGAGCCACTACTGCCAAT

CCGACTGGCACATTTGCAGGTAGCTCGTTTCCGGGAAATGATTATGCA

TTCGTCCGAACAGGGGCAGGAGTAAATTTGCTTGCCCAAGTCAATAAC

TACTCGGGCGGCAGAGTCCAAGTAGCAGGACATACGGCCGCACCAGTT

GGATCTGCTGTATGCCGCTCAGGTAGCACTACAGGTTGGCATTGCGGA

ACTATCACGGCGCTGAATTCGTCTGTCACGTATCCAGAGGGAACAGTC

CGAGGACTTATCCGCACGACGGTTTGTGCCGAACCAGGTGATAGCGGA

GGTAGCCTTTTAGCGGGAAATCAAGCCCAAGGTGTCACGTCAGGTGGT

TCTGGAAATTGTCGGACGGGGGGAACAACATTCTTTCAACCAGTCAAC

CCGATTTTGCAGGCTTACGGCCTGAGAATGATTACGACTGACTCTGGA

AGTTCCCCTGCTCCAGCACCTACATCATGTACAGGCTACGCAAGAACG

TTCACAGGAACCCTCGCAGCAGGAAGAGCAGCAGCTCAACCGAACGGT

AGCTATGTTCAGGTCAACCGGAGCGGTACACATTCCGTCTGTCTCAAT

GGACCTAGCGGTGCGGACTTTGATTTGTATGTGCAGCGATGGAATGGC

AGTAGCTGGGTAACCGTCGCTCAATCGACATCGCCGGGAAGCAATGAA

ACCATTACGTACCGCGGAAATGCTGGATATTATCGCTACGTGGTTAAC

GCTGCGTCAGGATCAGGAGCTTACACAATGGGACTCACCCTCCCCTGA

In the above sequence, bold indicates the DNA that encodes the mature protease, standard font indicates the leader sequence, and the underline indicates the N-terminal and C-terminal prosequences.
Expression of the Synthetic ASP Gene Expression of the synthetic ASP gene is described in U.S. patent application Ser. No. 10/576,331, which is incorporated herein by reference, in its entirety.

Example 4

Production of Combinatorial Mutants and Multiple Mutation Libraries

In this Example, methods used to construct combinatorial mutants and multiple mutation libraries are described.
Construction of Combinatorial Mutants Construction of combinatorial mutants of ASP is described in U.S. patent application Ser. No. 10/576,331, which is incorporated herein by reference, in its entirety.
Multiple Mutation Library Construction The multiple mutation library was constructed as outlined in the Stratagene QCMS kit, with the exception of the primer concentration used in the reactions. Specifically, 1 μL of the methylated, purified pUC18-ASP plasmid (about 70 ng) was mixed with 154, of sterile distilled water, 1.5 μL of dNTP, 2.5 μL of 10× buffer, 1 μL of the enzyme blend and 1.0 μL mutant primer mix (for a total of 100 μmol of primers). The primer mix was prepared using 10 μL of each of the eighteen mutant primers (100 pmol/L); adding 50 ng of each primer for the library as recommended by Stratagene, resulted in fewer mutations in a previous round of mutagenesis. Thus, the protocol was modified in the present round of mutagenesis to include a total of 100 μmol of primers in each reaction. The cycling conditions were 95° C. for 1 min, followed by 30 cycles of 95° C. for 1 min, 55° C. for 1 min, and 65° C. for 12 min, in an MJ Research PTC2-200 thermocycler using thin-walled 0.2 mL PCR tubes. The reaction product was digested with 1 μL of DpnI from the QCMS kit by incubating at 37° C. overnight. An additional 0.5 μL of DpnI was added, and the reaction was incubated for 1 hour.

Subsequently, the library DNA (mutagenized single stranded pUC18-ASP product) was electroporated to electro-competent E. coli cells (Invitrogen, cat. no C4040-52, One Shot® TOP 10 Electrocomp™ E. coli, dam+) and selective growth on agar plates containing 100 mg/L ampicillin resulted in the ASP multiple mutation library in E. coli cells. Colonies (tens of thousands) were harvested and the Qiagen spin miniprep DNA kit (cat. No. 27106) was used for preparing the plasmid DNA by the steps outlined in the Qiagen miniprep kit manual. The miniprep DNA was eluted with 50 uL of Qiagen buffer EB provided in the kit.

Miniprep DNA was digested using the PstI and HindIII DNA restriction enzymes. The ASP library fragment mix (PstI×HindIII) was gel purified and cloned in the 4154 base-pair HindIII×PstI pHPLT vector fragment by a ligase reaction using Invitrogen T4 DNA Ligase (Cat. No. 15224-025), utilizing Invitrogen's protocol as recommended for general cloning of cohesive ends). In another approach, synthetic ASP library fragments were produced by GeneArt. These ASP library fragments were also digested with PstI and HindIII, purified and cloned in the 4154 basepair HindIII×PstI pHPLT vector fragment by a ligase reaction.

To transform the ligation reaction mix directly into Bacillus cells, the library DNA (ASP library fragment mix cloned in pHPLT) was amplified using the TempliPhi kit (Amersham cat. #25-6400). For this purpose, 1 μL of the ligation reaction mix was mixed with 5 μL of sample buffer from the TempliPhi kit and heated for 3 minutes at 95° C. to denature the DNA. The reaction was placed on ice to cool for 2 minutes and then spun down briefly. Next, 5 μL of reaction buffer and 0.2 μL of phi29 polymerase from the TempliPhi kit were added, and the reactions were incubated at 30° C. in an MJ Research PCR machine for 4 hours. The phi29 enzyme was heat inactivated in the reactions by incubation at 65° C. for 10 min in the PCR machine.

For transformation of the libraries into Bacillus, 0.1 μL of the TempliPhi amplification reaction product was mixed with 500 μL of competent B. subtilis cells (ΔaprE, ΔnprE, oppA, ΔspoIIE, degUHy32, ΔamyE::(xylR,pxylA-comK) followed by vigorous shaking at 37° C. for 1 hour and 100 and 500 μL was plated on HI-agar plates containing 20 ppm neomycin sulfate (Sigma, Cat. No. N-1876; contains 732 μg neomycin per mg) and 0.5% skim milk. Ninety-five clones from the library were picked for sequencing.

The mutagenesis worked well, in that only 14% of the clones were equal to the backbone sequence (ASP with R014I-A064K-T086K-T116E-R123F), and about 3% of clones had extra mutations. The remaining of the sequenced clones (72%) were all mutants, and of these about 94% were unique mutants. The sequencing results for the library are provided below in Table 4-1.

TABLE 4-1

Variants of ASP with R014I-A064K-T086K-T116E-R123F

| | | | | |
|---|---|---|---|---|
| G54D | | | | |
| N24A | | | | |
| N24Q | | | | |
| N24T | | | | |
| N67S | | | | |
| R127K | | | | |
| R159F | | | | |
| R159K | | | | |
| R159K | | | | |
| R159N | | | | |
| R159N | | | | |
| G78D | R159F | | | |
| N24Q | R35E | | | |
| N67S | R159E | | | |
| R127K | R159E | | | |
| R127K | R159K | | | |
| R127K | R159N | | | |
| R127Q | R159K | | | |
| R35D | R159E | | | |
| R35D | R159K | | | |
| R35E | R159K | | | |
| G54D | R127K | R159K | | |
| G78D | R127K | R159K | | |
| G78D | R127K | R159E | | |
| G78D | R127Q | R159K | | |
| N24A | N67A | R159K | | |
| N24A | N67S | R159K | | |
| N24E | R35D | G78D | | |
| N24T | N67S | R159E | | |
| N67L | G78D | R159K | | |
| R35D | G78D | R159K | | |
| N24A | R35E | G78D | R159N | |
| N24D | R35D | G78D | R159F | |
| N24E | G54D | G78D | R159K | |
| N24E | R35D | G78D | R127K | R159N |
| N24Q | G54D | G78D | R159N | |
| N24Q | N67L | G78D | R159E | |
| N24Q | R35D | R127K | R159K | |
| N24T | R35D | G78D | R159K | |
| N24T | R35D | G78D | R159K | |
| N67S | G78D | R127K | R159K | |
| R35D | G78D | R127K | R159E | |
| R35D | G78D | R127K | R159N | |
| R35D | G78D | R127Q | R159K | |
| R35E | G54D | N67A | R159F | |

TABLE 4-1-continued

Variants of ASP with R014I-A064K-T086K-T116E-R123F

| | | | | | |
|---|---|---|---|---|---|
| R35E | N67S | G78D | R127Q | | |
| N24A | G54D | N67S | G78D | R159F | |
| N24A | R35D | N67A | G78D | R159F | |
| N24Q | R35D | N67L | G78D | R159K | |
| N24Q | R35D | N67L | G78D | R159N | |
| N24Q | R35D | N67S | R127K | R159E | |
| N24Q | R35E | N67A | R127K | R159E | |
| N24Q | R35E | N67A | G78D | R159E | |
| N24T | N67A | G78D | R127Q | R159N | |
| N24T | R35E | N67A | G78D | R127Q | |
| R35E | G54D | N67S | G78D | R159K | |
| N24A | G54D | N67S | G78D | R127K | R159K |
| N24A | R35E | N67S | G78D | R127K | R159K |
| N24E | R35E | G54D | N67S | R127K | R159N |
| N24Q | R35D | N67S | G78D | R127K | R159F |
| N24T | G54D | N67S | G78D | R127Y | R159E |
| N24E | R35E | G54D | N67S | G78D | R127K R159K |

Example 5

Correlation of Deleterious Mutations for Multiple Properties

In this Example, the principle that deleterious mutations for any property are correlated with deleterious mutations for every other property, regardless of correlations of the properties is exemplified. As indicated herein, only a small number of positions (5-10%) have mutations that are bad for all properties. These positions define the fold and are conserved in evolution. The implication of this is that although identification of beneficial mutations for any property requires a truly predictive screen for that property, identification of mutations likely to be deleterious for any property can be accomplished using any screen, including but not limited to the methods provided herein.

The variant enzymes (ASP, ACT, and NPRe) were produced as described herein and within U.S. patent application Ser. Nos. 10/576,331, 10/581,014, 11/581,102, and 11/583,334, all of which are incorporated by reference in their entirety. The Tables below provide pairwise comparisons of the numbers of variants with more than 5% wt activity and less than 5% activity for each of two properties, along with correlation coefficients for the two properties. The assay systems used in this Example are also provided in these applications. The properties used herein were casein activity (CAS), keratin activity (KER), AAPF activity (AAPF), LAS stability (LAS) and thermal stability for ASP; and peracid fromation (PAF) and peracid degradation (PAD) for ACT.

As indicated in the following Tables, the only properties that were found to be correlated (correlation coefficients>0.5) were CAS, KER and AAPF for ASP. All of the others were not correlated (correlation coefficient<0.3). In spite of the fact that the properties were not correlated, the probability that a mutation would be deleterious for the two properties is much higher than expected by chance. In the Table, the calculated ratios of observed numbers of variants expected based on chance are provided. Numbers that are greater than 1 indicate positive correlations, and numbers that are less than 1 indicate negative correlations.

TABLE 5-1

CAS and KER Comparison Results for ASP

| | Observed | | Expected | | |
|---|---|---|---|---|---|
| Value | CAS | KER | CAS | KER | Observed/Expected |
| <=5% | 892 | 674 | 31% | 24% | |
| >5% | 1959 | 2177 | 69% | 76% | |
| both >5% | 1877 | 66% | 1496 | 52% | 1.25 |
| one >5% | 382 | 13% | 1144 | 40% | 0.33 |
| Both <=5% | 592 | 21% | 211 | 7% | 2.81 |
| at least one >5% | 2259 | 79% | 2640 | 93% | 0.86 |

TABLE 5-2

CAS and AAPF Comparison Results for ASP

| | Observed | | Expected | | |
|---|---|---|---|---|---|
| Value | CAS | AAPF | CAS | AAPF | Observed/Expected |
| <=5% | 892 | 1263 | 31% | 44% | |
| >5% | 1959 | 1588 | 69% | 56% | |
| both >5% | 1576 | 55% | 1091 | 38% | 1.44 |
| one >5% | 395 | 14% | 1365 | 48% | 0.29 |
| Both <=5% | 880 | 31% | 395 | 14% | 2.23 |
| at least one >5% | 1971 | 69% | 2456 | 86% | 0.80 |

TABLE 5-3

CAS and LAS Comparison Results for ASP

| | Observed | | Expected | | |
|---|---|---|---|---|---|
| Value | CAS | LAS | CAS | LAS | Observed/Expected |
| <=5% | 892 | 1450 | 31% | 51% | |
| >5% | 1959 | 1401 | 69% | 49% | |
| both >5% | 1393 | 49% | 963 | 34% | 1.45 |
| one >5% | 574 | 20% | 1435 | 50% | 0.40 |
| Both <=5% | 884 | 31% | 454 | 16% | 1.95 |
| at least one >5% | 1967 | 69% | 2397 | 84% | 0.82 |

TABLE 5-4

CAS and Thermal Stability Comparison Results for ASP

| | Observed | | Expected | | |
|---|---|---|---|---|---|
| Value | CAS | THER | CAS | THER | Observed/Expected |
| <=5% | 892 | 1198 | 31% | 42% | |
| >5% | 1959 | 1653 | 69% | 58% | |
| both >5% | 1508 | 53% | 1136 | 40% | 1.33 |
| one >5% | 596 | 21% | 1340 | 47% | 0.44 |
| Both <=5% | 747 | 26% | 375 | 13% | 1.99 |
| at least one >5% | 2104 | 74% | 2476 | 87% | 0.85 |

TABLE 5-5

KER and AAPF Comparison Results for ASP

| | Observed | | Expected | | |
|---|---|---|---|---|---|
| Value | KER | AAPF | KER | AAPF | Observed/Expected |
| <=5% | 674 | 1263 | 24% | 44% | |
| >5% | 2177 | 1588 | 76% | 56% | |
| both >5% | 1566 | 55% | 1213 | 43% | 1.29 |
| one >5% | 633 | 22% | 1340 | 47% | 0.47 |
| Both <=5% | 652 | 23% | 299 | 10% | 2.18 |
| at least one >5% | 2199 | 77% | 2552 | 90% | 0.86 |

TABLE 5-6

PAF and PAD Comparison Results for ACT

| Value | Observed | | Expected | | Observed/Expected |
| --- | --- | --- | --- | --- | --- |
| | PAF | PAD | PAF | PAD | |
| <=5% | 541 | 751 | 19% | 26% | |
| >5% | 2536 | 2326 | 89% | 82% | |
| both >5% | 2187 | 2069 | 77% | 73% | 1.06 |
| one >5% | 488 | 639 | 17% | 22% | 0.76 |

TABLE 5-6-continued

PAF and PAD Comparison Results for ACT

| Value | Observed | | Expected | | Observed/Expected |
| --- | --- | --- | --- | --- | --- |
| | PAF | PAD | PAF | PAD | |
| Both <=5% | 402 | 143 | 14% | 5% | 2.82 |
| at least one >5% | 2675 | 2708 | 94% | 95% | 0.99 |

What is claimed is:

1. A method for identifying at least two positions in a parent serine protease protein that can be altered to improve at least one property of interest relative to the parent serine protease comprising the steps of:
   a) providing a parent serine protease protein comprising an amino acid sequence according to SEQ ID NO: 2 and a site evaluation library of protein variants of said parent serine protease protein, wherein the site evaluation library comprises variants of the parent protein modified at one position of interest;
   b) testing said library of protein variants for at least two properties of interest in a test of interest, wherein the properties of interest are selected from the group consisting of charge, wash performance, hard surface cleaning performance, thermal stability, storage stability, detergent stability, substrate binding, enzyme inhibition, expression level, reaction rate, and substrate degradation;
   c) determining a performance index for said at least two properties of interest by dividing a value obtained for the protein variants and a value obtained for said parent protein in the test of interest to provide an apparent $\Delta\Delta G_{app}$ for the protein variants compared to said parent protein in the test of interest;
   d) selecting protein variants having a performance index greater than 1.1 for at least one property of said at least two properties of interest;
   e) determining a predicted performance index value for protein variants that combine mutations at at least two positions of interest from said protein variants selected in step (d), wherein the predicted performance index value for the variants that combine at least two mutations are obtained by adding the $\Delta\Delta G_{app}$ values for those mutations; and
   f) identifying from the predicted performance index value obtained in step (e), the protein variants that combine at least two mutations and which possess a first property that is improved relative to the parent protein and a second property that is at least 90% of that of the parent protein, thereby providing a library of protein variants that have at least two properties of interest, wherein said parent protein and said protein variant are each a component of a detergent composition.

2. The method of claim 1, wherein said wash performance is tested in a detergent composition formulated into a powdered or liquid detergent having a pH of between 5 and 12.0.

* * * * *